(12) United States Patent
Thor et al.

(10) Patent No.: US 7,935,077 B2
(45) Date of Patent: May 3, 2011

(54) THROMBECTOMY CATHETER DEPLOYMENT SYSTEM

(75) Inventors: Eric Joel Thor, Arden Hills, MN (US); Michael John Bonnette, Minneapolis, MN (US); Nicole Jaye Aasen, Minneapolis, MN (US); Martyn Stuart Abbott, Dallas, TX (US); Douglas James Ball, Coon Rapids, MN (US); Walter Charles Croll, Maplewood, MN (US); David Charles Cummings, Richardson, TX (US); Chad Nicholas Grant, San Diego, CA (US); Mark Alfred Hilse, Ham Lake, MN (US); James Fredrick Karpinski, Blaine, MN (US); Daniel Joseph Kneip, Anna, TX (US); Jeffrey William Rogers, Plano, TX (US); Ernest Ralph Scherger, III, Center City, MN (US); John Lloyd Teschendorf, Lino Lakes, MN (US); Stephen Earl Weisel, Montrose, MN (US); David Woodruff West, Richardson, TX (US)

(73) Assignee: Medrad, Inc., Indianola, PA (US)

( * ) Notice: Subject to any disclaimer, the term of this patent is extended or adjusted under 35 U.S.C. 154(b) by 982 days.

(21) Appl. No.: 11/237,558

(22) Filed: Sep. 28, 2005

(65) Prior Publication Data
US 2007/0073233 A1  Mar. 29, 2007

(51) Int. Cl.
*A61M 31/00* (2006.01)
*A61N 1/30* (2006.01)
(52) U.S. Cl. .............................. 604/67; 604/19; 604/65
(58) Field of Classification Search ............... 604/14, 604/19, 65–67, 319–320
See application file for complete search history.

(56) References Cited

U.S. PATENT DOCUMENTS

| | | | |
|---|---|---|---|
| 2,464,283 A | 3/1949 | Adams | |
| 3,700,360 A | 10/1972 | Shaddock | |
| 4,065,230 A | 12/1977 | Gezari | |
| 4,778,356 A | 10/1988 | Hicks | |
| 4,821,761 A | 4/1989 | Aid et al. | |
| 4,846,636 A * | 7/1989 | Danby et al. | 417/413.1 |
| 4,892,279 A | 1/1990 | Lafferty et al. | |
| 4,925,444 A | 5/1990 | Orkin et al. | |
| 5,529,463 A | 6/1996 | Layer et al. | |

(Continued)

OTHER PUBLICATIONS

Final Rejection issued Aug. 11, 2008 in related U.S. Appl. No. 11/294,005.

(Continued)

*Primary Examiner* — Nicholas D Lucchesi
*Assistant Examiner* — Rebecca E Eisenberg
(74) *Attorney, Agent, or Firm* — David Schramm

(57) ABSTRACT

A thrombectomy catheter deployment system which greatly simplifies setup procedures and operation of a thrombectomy catheter includes a stand alone drive unit and a disposable pump/catheter assembly which is manually placed into a carriage assembly in the drive unit. The pump/catheter assembly has a plurality of preconnected components including tubular structure and a thrombectomy catheter connected thereto and is transported into or out of the interior of the drive unit for automatic high pressure pump piston head engagement or disengagement with a reciprocating linear actuator and for automatic engagement or disengagement of an effluent waste tube with a roller pump. A barcode reader senses specific operational data pertaining to an individual pump and provides an interface for operation of the reciprocating linear actuator. A bubble trap incorporated for effective debubbling of saline solution is closely coupled to an insert molded pump having an improved valve arrangement. A spiked bag with large tubing is incorporated for bubble-free transfer of saline.

21 Claims, 28 Drawing Sheets

U.S. PATENT DOCUMENTS

| | | | |
|---|---|---|---|
| 5,536,242 A | | 7/1996 | Willard et al. |
| 5,544,660 A | | 8/1996 | Crowley |
| 5,681,285 A | * | 10/1997 | Ford et al. .................... 604/151 |
| 5,827,229 A | | 10/1998 | Auth et al. |
| 5,879,361 A | | 3/1999 | Nash |
| 6,071,269 A | * | 6/2000 | Schnell et al. ................ 604/406 |
| 6,676,627 B1 | | 1/2004 | Bonnette et al. |
| 6,695,803 B1 | | 2/2004 | Robinson et al. |
| 6,719,717 B1 | | 4/2004 | Johnson et al. |
| 6,926,726 B2 | * | 8/2005 | Drasler et al. ................ 606/159 |
| 6,936,056 B2 | | 8/2005 | Nash et al. |
| 2004/0069709 A1 | | 4/2004 | Brugger et al. |
| 2005/0177096 A1 | * | 8/2005 | Bollish et al. .................. 604/65 |
| 2006/0052664 A1 | * | 3/2006 | Julian et al. ................... 600/146 |
| 2007/0129679 A1 | | 6/2007 | Bonnette |

OTHER PUBLICATIONS

Angiojet Product Manual, Possis Medical, Inc., May 7, 2005.

International Search Report issued in corresponding International Patent Application PCT/US06/36684.

Final Rejection Mailed Aug. 11, 2009 in corresponding U.S. Appl. No. 11/294,005.

* cited by examiner

THROMBECTOMY CATHETER DEPLOYMENT SYSTEM

CROSS REFERENCES TO RELATED APPLICATIONS

None.

BACKGROUND OF THE INVENTION

1. Field of the Invention

In the human body blockages in blood vessels, arteries and the like often oppose the free flow of blood therein, one such blockage of which is thrombus. Thrombus is coagulated blood that is developed in vivo. Thrombus blocks blood flow to living tissue leading to ischemia and eventually tissue death. Depending on the end organ and the amount of blocked blood flow, the effects of thrombus can range from unnoticeable to patient death. Thrombus residing in a variety of native vessels and grafts can be treated. The occurrence and presence of thrombus occurs in several ways. First, it occurs in coronary procedures where thrombus is associated with myocardial infarction or heart attack. Thrombus is also common in older saphenous vein bypass grafts. Second, peripheral artery interventional procedures can encounter thrombus as well. The use of synthetic grafts and stents for the treatment of peripheral arterial disease can produce thrombus as a result of blood material interactions. Furthermore, thrombus can be formed resulting from the progression of the peripheral artery disease itself. As the artery becomes blocked with atherosclerotic material, thrombus can result as blood passes through the restricted diseased vessel. Venous thrombus can result from either vessel injury or hypercoagulable blood chemistry. Finally, interventional procedures themselves can create thrombus. Access to the patient's arterial vascular system is commonly accomplished via a femoral artery puncture. At the end of the procedure, the puncture site must be closed by either applying pressure until a natural thrombotic plug forms or using an arterial closure product which typically uses some sort of collagen plug or suture. In either case, thrombus can form at the puncture site and move down the femoral artery. Furthermore, during the interventional procedure itself, foreign materials such as catheters and guidewires are introduced into the patient's blood stream. The patient needs anticoagulants, typically heparin, to prevent the occurrence of thrombus. On occasion, inattention to activated clotting times can result in the occurrence of thrombus during the procedure. Third, other parts that have been treated by thrombectomy catheters include arterial-venous access grafts for hemodialysis patients. Thrombectomy catheters have proven effective in opening these grafts that occasionally become blocked with thrombus. Thrombectomy catheters have also been used in the venous system for deep vein thrombosis and occasionally in neurological venous applications. Finally, thrombectomy catheters have been clinically investigated in neurological arterial applications as well. In general, thrombectomy catheters have a potential application wherever thrombus forms in native arteries, veins and grafts. Having developed such thrombectomy catheters, there exists a need for a deployment system to allow simple and rapid use of a thrombectomy catheter and the devices supporting use of the thrombectomy catheter.

2. Description of the Prior Art

Comparison of Prior Art Devices to the Present Invention

Current thrombectomy catheter utilization devices consist of a drive unit, disposable components including a variety of sterile thrombectomy catheters, a transportable sterile pump, bubble detectors, a saline supply tube/bag spike assembly, a nonsterile waste or effluent collection bag, and other associated components. Often, the use of such devices is overall cumbersome involving a large number of setup steps required for preparation and use. The current setup steps are roughly as follows (assuming the drive unit is on):

(1) open sterile package for the pump set;
(2) do a sterile exchange to hand off the catheter connection end of the pump supply line to the sterile technician;
(3) preclamp a Roberts clamp for the saline supply tube line;
(4) load the pump into the capture block while simultaneously loading the pump piston head into a reciprocating ram;
(5) spike a heparinized bag of saline;
(6) install the saline supply tube into an inlet bubble detector;
(7) unclamp the bag spike Roberts clamp to enable the pump to become primed;
(8) open the effluent collection bag packaging and remove the effluent collection bag;
(9) attach the effluent return tube to the proximal end of the pump supply line effluent connection;
(10) hang the effluent collection bag on the side of the drive unit;
(11) install the effluent waste tube through the roller pump;
(12) close the roller pump cover;
(13) push the effluent waste tube into the outlet bubble detector just proximal to the roller pump;
(14) select the catheter mode on the drive unit;
(15) open the catheter sterile packaging;
(16) do a sterile exchange to hand off the entire catheter to the sterile technician;
(17) connect the high pressure connection from the pump supply line to the catheter;
(18) connect the effluent Luer connection from the supply line to the catheter; and,
(19) submerge the catheter tip in a bowl of sterile saline and operate a drive unit foot switch to prime the catheter.

Compare this to the thrombectomy catheter deployment system, the present invention, having a plurality of preconnected components where the setup consists of:

(1) opening sterile package for the pump and catheter assembly;
(2) doing a sterile exchange to hand off the catheter to the sterile technician;
(3) loading the pump/catheter assembly into a capture block in the drive unit (this will automatically position the attached effluent collection bag in a supported position to the front of the drive unit);
(4) spiking a heparinized bag of saline; and,
(5) submerging the catheter tip in a bowl of sterile saline and operating the drive unit to prime the catheter.

Other differences concern the drive unit itself. Current drive units are electrically operated analog devices with a very small number of available modes. The drive unit of the thrombectomy catheter deployment system uses digital technology to enable thousands of modes. The analog technology in current drive units require calibration of several pot style resistors to modify an existing mode to produce a new mode profile. This would be conducted in the field by a service technician. The thrombectomy catheter deployment system inputs the mode information automatically via a barcode or radio frequency identification technology so no hardware or software changes are required by any field service staff when new modes are added or deleted from the thrombectomy catheter deployment system operation portfolio.

Current generation drive units have sequentiality built into the setup steps. The drive unit must turn on and go through self-test prior to placing the pump into the capture block. The pump must be loaded prior to spiking the saline supply bag, etc. Compare this to the instant invention where the disposable pump/catheter assembly can be loaded prior to turning on the drive unit. Furthermore, the saline supply bag can be spiked prior to or after loading the pump. The only step that requires sequentiality is priming the catheter (the saline supply bag must be spiked and the pump must be in the drive unit in order to operate the catheter so that the catheter can be primed). Current thrombectomy utilization devices have alarm conditions that hinder the setup procedure including detection of air from the saline supply tube/bag spike assembly. For example, forgetting to preclamp the Roberts clamp on the drive often results in air being introduced into the pump and trips an alarm. The thrombectomy catheter deployment system, the present invention, uses a saline supply tube/bag spike assembly and a drive unit which prevent air introduction into the pump and includes a mechanism in the drive unit to correct itself by a repeated pump prime action to remove air from the pump; i.e., the drive unit burps the pump if air is in the pump.

Current thrombectomy catheter utilization devices involve substantially a two-handed installation maneuver where a pump body is aligned within a capture block in the drive unit while a piston head of the pump is simultaneously loaded into a receptor in a reciprocating linear actuator. Each manual maneuver requires devoted attention and coordination by the operator. Contrast this to the thrombectomy catheter deployment system, the present invention, where a preconnected pump/catheter assembly is simply placed in a capture block whereupon, by command, the capture block and the preconnected pump/catheter assembly is positioned to cause automatic engagement of the pump piston head with a reciprocating linear actuator without any extraordinary effort by the operator.

Combining the thrombectomy catheter and pump enables positioning of the high pressure saline supply tube inside the effluent return tube in coaxial fashion, thereby reducing parts and bulk, making it easier to handle and package. The high pressure saline supply tube is a metal hypotube that delivers saline from the output of the pump to the thrombectomy catheter. The high pressure saline supply tube extends through a connection manifold assembly and through the lumen of the effluent return tube. The effluent return tube delivers macerated thrombus/blood back to an effluent collection bag via the connection manifold assembly and an effluent waste tube. The connection manifold assembly includes a plastic connector on a proximal port. The connection manifold assembly serves as a junction between the effluent return tube and the effluent waste tube.

Current manifolds of the thrombectomy catheter utilization devices include four ports: a hemostatic valve for a guidewire, a port for the catheter tube, a port for the supply tube/catheter hypotube, and a port for effluent. The connection manifold assembly of the thrombectomy catheter deployment system, the present invention, only requires three ports: a proximal port for the hemostatic valve, a distal port for the effluent waste tube, and a distal port for the coaxially aligned high pressure saline supply tube/effluent return tube. Since the high pressure saline supply tube is inside the effluent return tube, there is only one port on the connection manifold assembly needed instead of the two on a current art manifold. Furthermore, removing a port removes the ability of the physician to inject contrast through the catheter. This is a safety concern, since contrast injection through the catheter has been associated with unintended air introduction into the patient. Also, combining the pump and catheter as an assembly minimizes the ports on the connection manifold assembly and prevents unauthorized fluid introduction.

Occasionally, a pump with a sticky inlet check ball will lead to priming difficulties. Often, current pumps have valves utilizing a stainless steel ball in communication with a high tolerance peened metal surface of a ball seat to serve as an inlet check valve. The ball seat in each pump is peened with a ball to create an ideal sealing surface. Peening of the ball seat is critical. If the surface is overpeened by using excessive force with an excessively small ball for peening, the ball can become stuck in the ball seat. If the surface is not sufficiently peened, such as by an excessively large ball with insufficient force, the check ball will not seal properly and flow will go out past the check ball rather than out the pump outlet to the thrombectomy catheter. The design of an insert molded pump in the thrombectomy catheter deployment system is intended to prevent the incidence of something called sticky check balls. The insert molded pump of the present invention has a much larger stainless steel ball (0.172 inch versus 0.078 inch diameter for example and illustration), and the ball seals against a molded plastic seat to prevent the occurrence of sticky check balls. The use of an insert molded pump also provides for more economy and size and tolerance predictability.

SUMMARY OF THE INVENTION

The general purpose of the present invention is to provide a thrombectomy catheter deployment system.

Current thrombectomy catheter utilization devices include a nondisposable drive unit which accommodates disposable components such as a catheter, a pump, a waste bag, bubble traps, a bag spike, and other closely associated components which are loaded into or closely associated with the drive unit support structures which are used to operate a thrombectomy catheter where the use of such is characterized by customers as a relatively difficult to use system. The discovery of thrombus during an interventional procedure is often an unexpected and emergency situation. The ability to set up the thrombectomy catheter utilization devices as rapidly as other common interventional tools would be highly beneficial. For example, balloon catheters take only seconds to prime. Although a well trained individual can set up a thrombectomy catheter utilization device in less than a minute, current thrombectomy catheter utilization devices have limited tolerance for nonsequential setup steps. Any miscue by the user can easily extend the setup time beyond one minute, and in some cases the setup time can exceed 30 minutes, especially for untrained personnel. In an effort to dramatically improve the ease of use and rapid deployment for a thrombectomy catheter utilization device, the thrombectomy catheter deployment system, the present invention, removes many setup steps and alarms, such as found in prior art thrombectomy catheter utilization devices. Fundamental to the thrombectomy catheter deployment system is the combination of a pump and a thrombectomy catheter, as well as other closely associated components broadly known as a disposable pump/catheter assembly. This combination in itself removes multiple assembly steps for the disposable pump/catheter assembly. Most importantly, the disposable pump/catheter assembly is incorporated into use with a nondisposable onboard roller pump to ensure that isovolumetric flow is achieved. Isovolumetric flow means that the flow rate of the effluent flow (blood, saline, and macerated thrombus) equals the flow rate of saline infused into the patient. The combination of the pump and catheter enables each disposable assembly to be tested to ensure that the fluid restrictions are appropriate to achieve this balanced flow. Typically, thrombectomy catheters remove more flow from the patient than the infused flow rate. Consequently, the roller pump is utilized to function as a fluid restrictor.

Other detractions to the quick and simple utilization of the thrombectomy catheter utilization devices include realization and observation of operating parameters requiring operator intervention or input of such information being referred to as operating mode which conveys particulars concerning pump stroke length, downstroke speed, acceleration time, deceleration time, upstroke speed, and total cycle time. Operating mode is the position versus time curve for the pump ram. It is clearly important information for operating a thrombectomy catheter utilization device, but many users have no idea what mode information means. The idea of an operating mode is foreign to the user. Therefore, barcode information regarding the pump and the catheter are displayed on the pump and automatically detected by the drive unit of the thrombectomy catheter deployment system without user intervention. Such collective information regarding the pump and catheter combination is included on the barcode for operation of the particular pump and particular catheter combination as determined during the manufacturing process. Thereby, calibration between the pump/catheter assembly with the control circuitry of the drive unit is automatic, requiring no operator action. The use of a barcode enables essentially unlimited numbers of modes to be conveyed to the drive unit since the aforementioned mode particulars will all be part of the barcode information. Thus, no field upgrade is needed for either hardware or software when a new mode is developed for a new catheter. Without the combination of the pump/catheter assembly, operation would be extremely difficult.

The mode information directs the drive unit to operate the pump at a flow rate appropriate to the attached catheter. The catheter is the primary fluid restrictor. Therefore, the catheter design is what determines which mode is appropriate. The mode is the flow rate versus time curve. For example, one could have a 0.5 sec. downstroke and a 0.5 sec. upstroke. Alternatively, one could have a 0.3 sec. downstroke and a 0.7 sec. upstroke. Both would give 60 strokes per minute, but are different modes. By combining the pump and catheter, the barcode information on the pump applies to the integral catheter.

The barcode is also an important feature for preventing unauthorized competitive products to be used on proprietary drive units of the instant invention. The safety of the thrombectomy catheter deployment system considers all aspects of the system including the disposable pump, disposable catheter, saline supply tube/bag spike assembly, effluent collection bag, and drive unit. The ability to use the barcode information to prevent unauthorized products from being used on the thrombectomy catheter deployment system is fundamental for ensuring safety and preventing the thrombectomy catheter deployment system drive unit from being damaged.

The general purpose of the present invention is a thrombectomy catheter deployment system. The thrombectomy catheter deployment system is designed to include structure to successfully deploy and support the use of an included thrombectomy catheter, wherein multiple, high velocity saline jets at the distal end of a catheter remove unorganized/(relatively fresh) thrombus from arteries and vascular grafts or percutaneously lyse and remove unorganized (relatively fresh) thrombus from arteries and vascular grafts. One of the main and central components of the thrombectomy catheter deployment system includes a broadly encompassing pump/catheter assembly which is disposable and of single use, having, in part, a thrombectomy catheter and connected pulsatile pump, various tubing, and an effluent collection bag. Another main and central component of the thrombectomy catheter deployment system is a drive unit which is nondisposable and which accommodates the pump/catheter assembly about or within the drive unit enclosure. The drive unit includes a carriage assembly and a reciprocating linear actuator, each for the accommodation of the pump/catheter assembly. The drive unit also includes an operator interface and other components essential for operation of the instant invention. The carriage assembly readily and simply accommodates the pump/catheter assembly, which is disposable, and positions the pump piston head of the pump for automatic connection to the reciprocating linear actuator. The reciprocating linear actuator drives the pump to pressurize saline and supply high pressure saline to the thrombectomy catheter. Jet streams are created at the distal tip of the catheter tube by high pressure saline being introduced through small orifices. The saline is sprayed out through the jet orifices indirectly into the vascular segment being treated. The high velocity saline jets are proximally directed and create a localized vacuum at the catheter tip that results in the entrainment, dissociation, and ultimate evacuation of blood, saline, and thrombus into an external effluent collection bag. The macerated thrombus is pushed through the evacuation lumen of the effluent return tube due to the dynamic pressure generated by proximally directed jets. Secondary flow patterns of fluid (blood, saline) created by the jets provide a disruption of the thrombus and assist in the delivery of thrombus fragments into the pathway of the proximally directed saline jets for further ablation and removal. The secondary flow provides sufficient mixing in the vessel to allow thrombus ablation and removal in a vessel that is larger in diameter than the catheter shaft.

The thrombectomy catheter deployment system uses isovolumetric flow where the effluent flow rate being evacuated from the vessel is the same as the infused flow rate of saline delivered to the thrombectomy catheter. In general, the effluent flow rate without a roller pump is larger than the infused flow rate. The thrombectomy catheter deployment system uses a roller pump on the effluent waste tube to apply a restriction to ensure that the effluent flow rate is the same as the infused flow rate. Also, the roller pump prevents blood flow through the thrombectomy catheter to the effluent collection bag during periods when the catheter tube is in the patient but the catheter tube is not being activated. The thrombectomy catheter deployment system uses an automatically engaging structure to engage the effluent waste tube with the roller pump. No extra user intervention is required to install the effluent waste tube into the roller pump engaging structure. The benefit of this approach for flow control is the elimination of user interaction to install the effluent waste tube in the roller pump assembly.

The drive unit contains a positionable carriage assembly and a specially designed reciprocating linear actuator that engages the pump piston head without user intervention. A capture block is included in a positionable carriage assembly. When the carriage assembly is extended to the open position, the pump/catheter assembly is manually placed into the capture block followed by closing of the carriage assembly. The reciprocating linear actuator contains spring pawls located in a pump connector, a capture mechanism, that enables the reciprocating linear actuator to vertically engage the pump piston head as the reciprocating linear actuator is lowered onto the pump piston head. The reciprocating linear actuator is the moving part of the drive unit that reciprocatingly moves the piston of the pump up and down to provide high pressure saline for use in the thrombectomy catheter. At the end of the procedure, sliding disengagement of the pump piston head from the pump connector of the reciprocating linear actuator occurs in a horizontal direction when the carriage assembly and capture block position the pump forward from the pump connector.

The thrombectomy catheter deployment system employs an insert molded pump. Insert molding the pump enables the pump to be made economically, while still maintaining adequate integrity. Molding the plastic and glass-filled nylon about a stainless steel insert enables the high tolerance fits to be created by the molding process rather than have high tolerance fits machined into the stainless steel parts. Insert molding the pump also reduces the weight of the pump, making the packaging easier, as generally packaging robustness needs to increase with increased weight of the packaged item. Finally, insert molding enables the elimination of several of the components, thus further reducing cost and complexity.

The thrombectomy catheter deployment system contains a barcode reader for automatic mode selection and for pertinent data regarding the individual catheter tube and individual pump and associated operating parameters. The need for service to upgrade the software on the drive unit for new catheter modes is eliminated as the information can be contained on the barcode. Also eliminated is the need for the customer to input the mode information. The barcode information is protected by a data protection scheme, computer redundancy check (CRC), that ensures that the mode information is input into the drive unit in a reliable fashion. Furthermore, a special alphanumeric sequence, or encryption technique, can be built into the barcode information to ensure that only authorized proprietary catheters and pumps are used in the thrombectomy catheter deployment system. Note that the barcode and the barcode reader may, in fact, be a radio-frequency transponder and reader or other equivalent digital tagging technology.

A bag spike and associated components are included which minimize bubble formation for use with a bubble trap. The bag spike is designed to prevent a continuous stream of bubbles from entering the pump. The bag spike uses a high flow spike, as well as larger inside diameter tubing, to reduce the fluid restriction between the bag and the pump. Furthermore, the bubble trap is positioned at the pump inlet. The bubble trap is designed with interior walls to enhance debubbling of the saline prior to the pump inlet. Therefore, if the bag spike or saline supply tube is perforated, any bubbles that enter the tube will be removed by the bubble trap. If the bubble trap itself were to develop a perforation, the saline would leak out rather than suck air into the trap since it is attached directly at the pump inlet and has sufficiently low fluid restriction.

According to one or more embodiments of the present invention, there is provided a thrombectomy catheter deployment system including a drive unit and a pump/catheter assembly. The drive unit includes necessary components providing for transporting of the drive unit, including wheels, a brake, and a handle, and also contains support devices for operation of the invention. Centrally located automatically opening doors accommodate movement of a carriage assembly inwardly and outwardly to and from the interior of the drive unit. The carriage assembly accommodates a manually-placed pump/catheter assembly which is transported into or out of the interior of the drive unit for automatic engagement with a reciprocating linear actuator. A user interface is incorporated at the upper region of the drive unit. The pump/catheter assembly includes a plurality of preconnected components including, but not limited to, a pump, a thrombectomy catheter, a bubble trap, a connection manifold assembly at the bubble trap, an effluent waste tube, an effluent collection bag, a saline supply tube, a bag spike, and a coaxial high pressure saline supply tube and effluent return tube connected to the thrombectomy catheter.

One significant aspect and feature of the present invention is a thrombectomy catheter deployment system which greatly simplifies setup procedures for deployment and operation of a thrombectomy catheter.

Another significant aspect and feature of the present invention is a thrombectomy catheter deployment system incorporating a drive unit and a pump/catheter assembly.

Another significant aspect and feature of the present invention is the use of a pump/catheter assembly which is disposable and which is one use.

Still another significant aspect and feature of the present invention is a thrombectomy catheter deployment system having a carriage assembly in a drive unit which accommodates a pump/catheter assembly.

Yet another significant aspect and feature of the present invention is the utilization of a pump/catheter assembly where the pump/catheter assembly has preconnected components including a pump, a thrombectomy catheter, a bubble trap, a connection manifold assembly at the bubble trap, an effluent waste tube, an effluent collection bag, a saline supply tube, a bag spike, and a coaxial high pressure saline supply tube and effluent return tube connected to the thrombectomy catheter.

Yet another significant aspect and feature of the present invention is the direct connection of a bubble trap to the pump of the pump/catheter assembly to effectively debubble saline solution.

A further significant aspect and feature of the present invention is the use of a pump/catheter assembly wherein the pump of the pump/catheter assembly is positioned by a carriage assembly for automatic capture or release of a pump piston head by a pump connector of a reciprocating linear actuator.

A further significant aspect and feature of the present invention is the outward positioning of a carriage assembly to cause release of a pump piston head from the pump connector.

A further significant aspect and feature of the present invention is the use of a pump/catheter assembly wherein the effluent waste tube of the pump/catheter assembly is automatically engaged or disengaged by a roller pump.

A further significant aspect and feature of the present invention is the use of a roller pump in engagement with an effluent waste tube to achieve isovolumetric flow control.

A still further significant aspect and feature of the present invention is the use of an insert molded pump incorporating close tolerance molded components including a molded check ball seat.

A further significant aspect and feature of the present invention is the incorporation of a barcode reader in a drive unit to read a barcode on a pump/catheter assembly.

A still further significant aspect and feature of the present invention is the use of barcode information to access data regarding the individual pump and the individual thrombectomy catheter of a pump/catheter assembly.

A still further significant aspect and feature of the present invention is the use of barcode information to reprogram the operation of the drive unit.

A still further significant aspect and feature of the present invention is the use of barcode information to hinder the use of unauthorized pump/catheter assemblies.

A further significant aspect and feature of the present invention is the use of a saline supply tube/bag spike assembly with large tubing incorporated for bubble-free transfer of saline.

Having thus briefly described the present invention and mentioned some significant aspects and features thereof, it is the principal object of the present invention to provide a thrombectomy catheter deployment system.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENT

Figure 1:
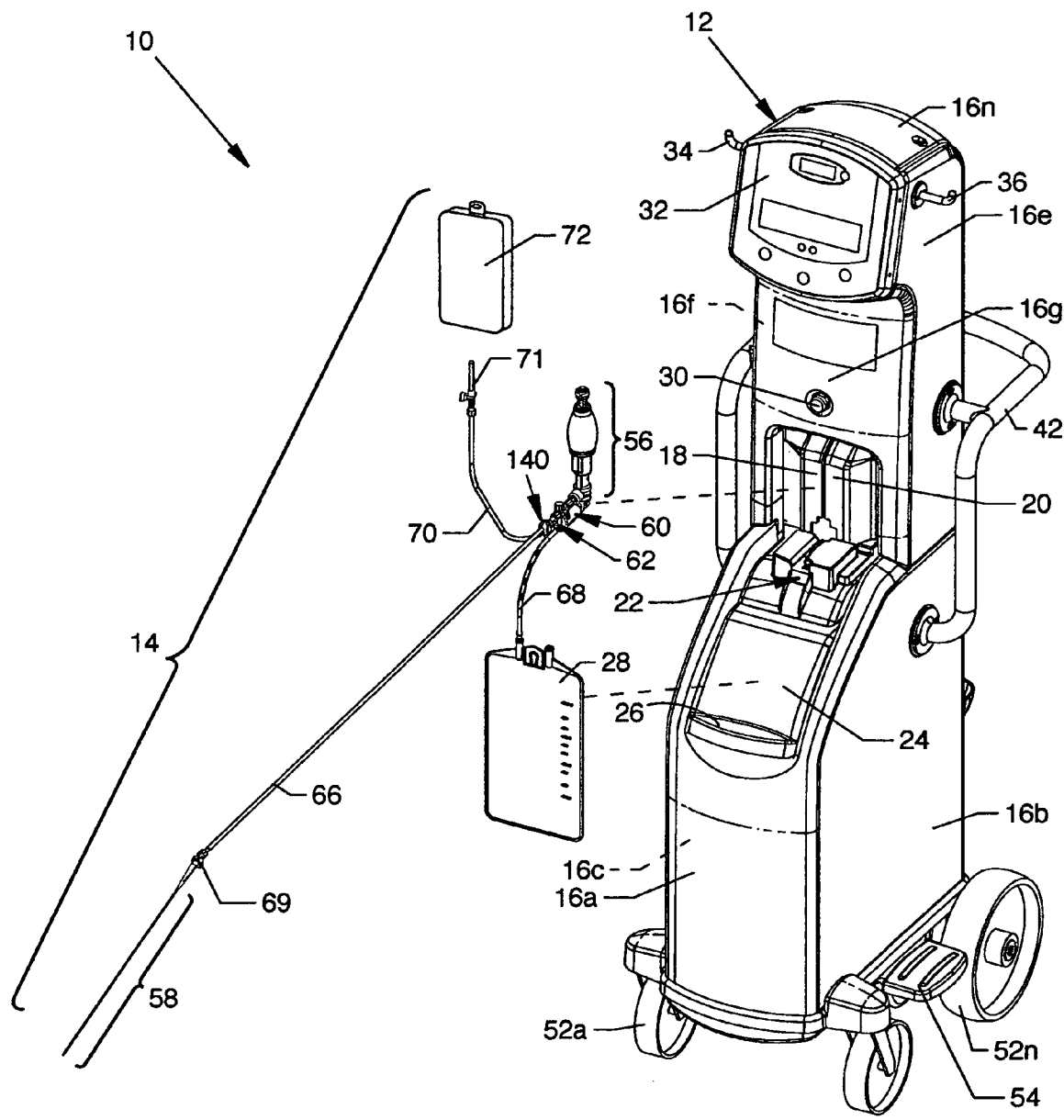
FIG. 1 is a view of a thrombectomy catheter deployment system, the present invention.

FIG. 1 is a view of a thrombectomy catheter deployment system 10, the present invention. Directly visible in the illustration are a drive unit 12 and a pump/catheter assembly 14 comprising the thrombectomy catheter deployment system 10. Shown on the drive unit 12 are a plurality of removable panels 16a-16n about and along the drive unit 12 enclosing structure exposed to view in FIG. 2. Centrally located in the drive unit 12 and aligned to the lower region of the panel 16g are automatically opening doors 18 and 20 which open to expose the interior of the drive unit 12 and the rear portion of a carriage assembly 22 also shown in FIG. 2. The front portion of the carriage assembly 22, which accommodates the pump/catheter assembly 14, is shown extending from the interior of the drive unit 12 beneath the closed doors 18 and 20. The carriage assembly 22 is rearwardly and forwardly positionable to the closed and open positions, respectively. A removable drip tray 24 is shown in oblique orientation located on the front of the drive unit 12 extending from below the carriage assembly 22 toward the panel 16a. The drip tray 24 and a receptacle 26, which is removable, located above panel 16a, collectively support and accommodate an effluent collection bag, such as effluent collection bag 28 of the pump/catheter assembly 14. A carriage assembly activation switch 30 located on panel 16g facilitates positioning of the carriage assembly 22 inwardly or outwardly. A user interface 32 including memory capabilities is located at the upper region of the drive unit 12 between the upper regions of the upper side panels 16e and 16f (FIG. 3). Saline bag hooks 34 and 36 extend through the panels 16e and 16f to secure to mounting pads 38 and 40, shown in FIGS. 4 and 2, respectively. A continuous handle 42 formed of tubing with appropriate mounting extensions secures through the panels 16f, 16c, 16e and 16b to secure to mounting pads 44, 46, 48 and 50 shown in FIGS. 4 and 2, respectively. A plurality of wheels 52a-52n and brake pedals 54 and 55 (FIG. 3) for wheel lockage are located at the lower region of the drive unit 12. The pump/catheter assembly 14 is shown apart from the drive unit 12 and includes a pump 56 and a thrombectomy catheter 58. Other components included in the pump/catheter assembly 14 are a bubble trap 60 attached directly to the pump 56, a connection manifold assembly 62 connected directly to the bubble trap 60, an effluent return tube 66 connected between the connection manifold assembly 62 and the thrombectomy catheter 58, a coaxially arranged high pressure saline supply tube 64 aligned inside the effluent return tube 66 attached between the output of the pump 56 and the thrombectomy catheter 58, a transition fixture 69 between the distal end of the effluent return tube 66 and the proximal end of the thrombectomy catheter 58, an effluent waste tube 68 connecting the effluent collection bag 28 to the connection manifold assembly 62, and a large diameter saline supply tube 70 having a bag spike 71 connecting a saline supply bag 72 to the connection manifold assembly 62 which communicates with the interior of the bubble trap 60. Other interconnections and features of the components of the pump/catheter assembly 14 are described later in detail.

Figure 2:
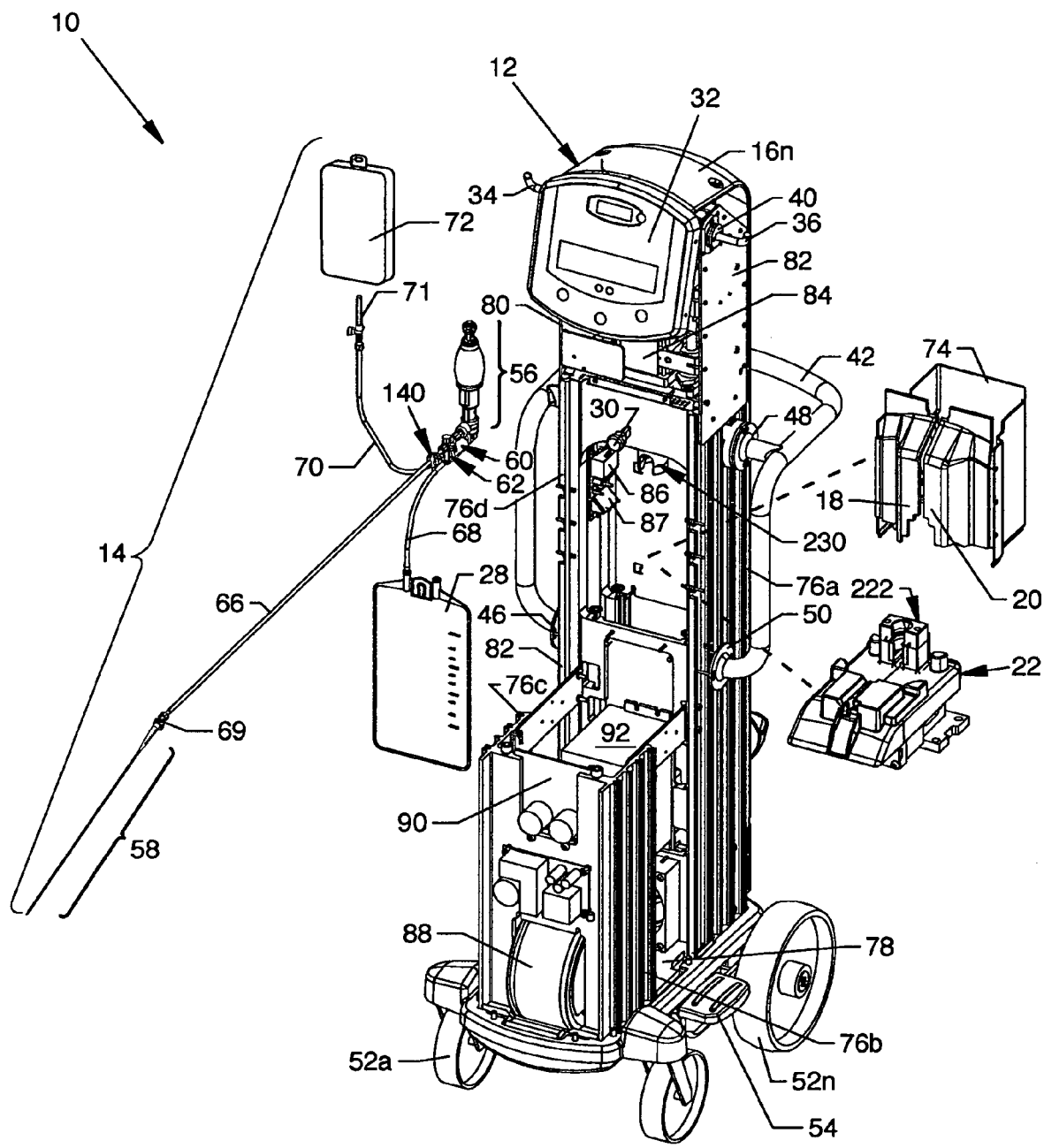
FIG. 2 is a view of the thrombectomy catheter deployment system where external panels of the drive unit have been removed to reveal components residing in the drive unit.
Figure 3:
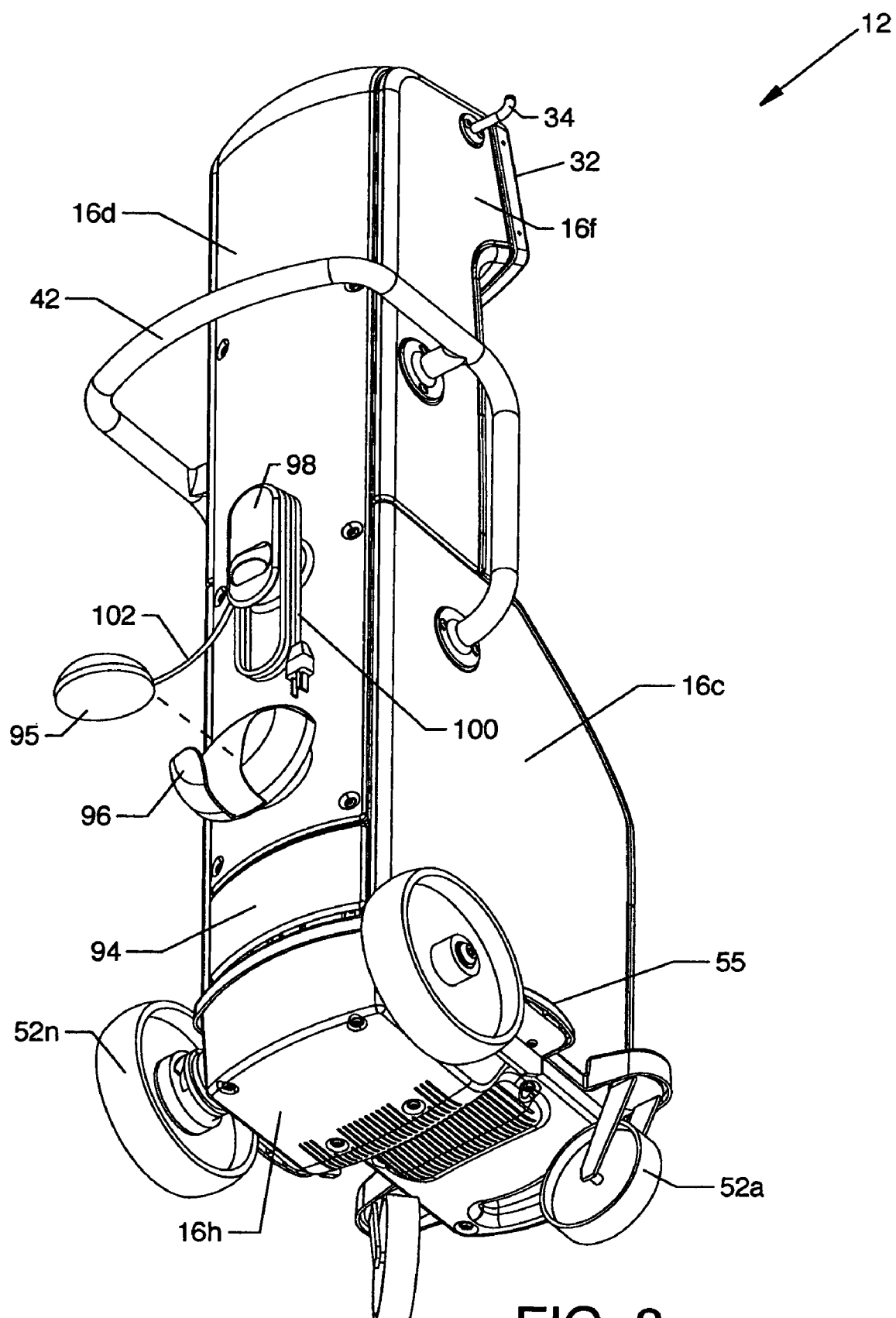
FIG. 3 is a rear view of the drive unit.

FIG. 2 is a view of the thrombectomy catheter deployment system 10 where the panels 16a-16n have been removed to reveal other components residing in the drive unit 12. The carriage assembly 22 and a splash guard 74, which serves as a mounting structure for the doors 18 and 20, are shown removed and distanced from the general structure of the drive unit 12. The splash guard 74 supports the doors 18 and 20, and with the doors 18 and 20 encompasses the majority of the area about the carriage assembly 22 to assist the drip tray 24 in containing any leaking fluids in and about the carriage assembly 22 and any associated enclosed or related portions of the pump/catheter assembly 14 by channeling any stray fluids into the removable receptacle 26. A plurality of configured support structures 76a-76d resembling heat sink structure extend vertically from a base 78 which serves as a mount for the wheels 52a-52n and associated structure. Vertically aligned panels 80 and 82 are attached to the upper regions of the support structures 76d and 76a for support of the user interface 32 and for serving as a mount for the mounting pads 38 (FIG. 4) and 40. A vertically oriented reciprocating linear actuator 84 is partially shown behind the user interface 32 mounted in support structure extending between the upper portions of the support structures 76a and 76d in the upper region of the drive unit 12 in vertical alignment with the carriage assembly 22 for subsequent automatic engagement of the pump 56 of the pump/catheter assembly 14, as later described in detail. Also attached to the inner surface of the support structure 76d is a barcode reader assembly 86 including a mirror 87 mounted at an angle which reads a barcode included on the pump 56 subsequent to insertion of the pump/catheter assembly 14. Also shown located suitably mounted in the lower regions of the drive unit 12 are an isolation transformer 88, a power supply 90 for electrical current stabilization, and a linear actuator controller 92.

FIG. 3 is a rear view of the drive unit 12 showing a rear access panel 94, a foot switch 95, a foot switch holder 96, and a hanger 98 for accommodation of an electrical supply cord 100 and a foot switch cord 102. The foot switch 95 is incorporated to be controlled by the physician operator in order to pressurize the thrombectomy catheter 58.

Figure 4:
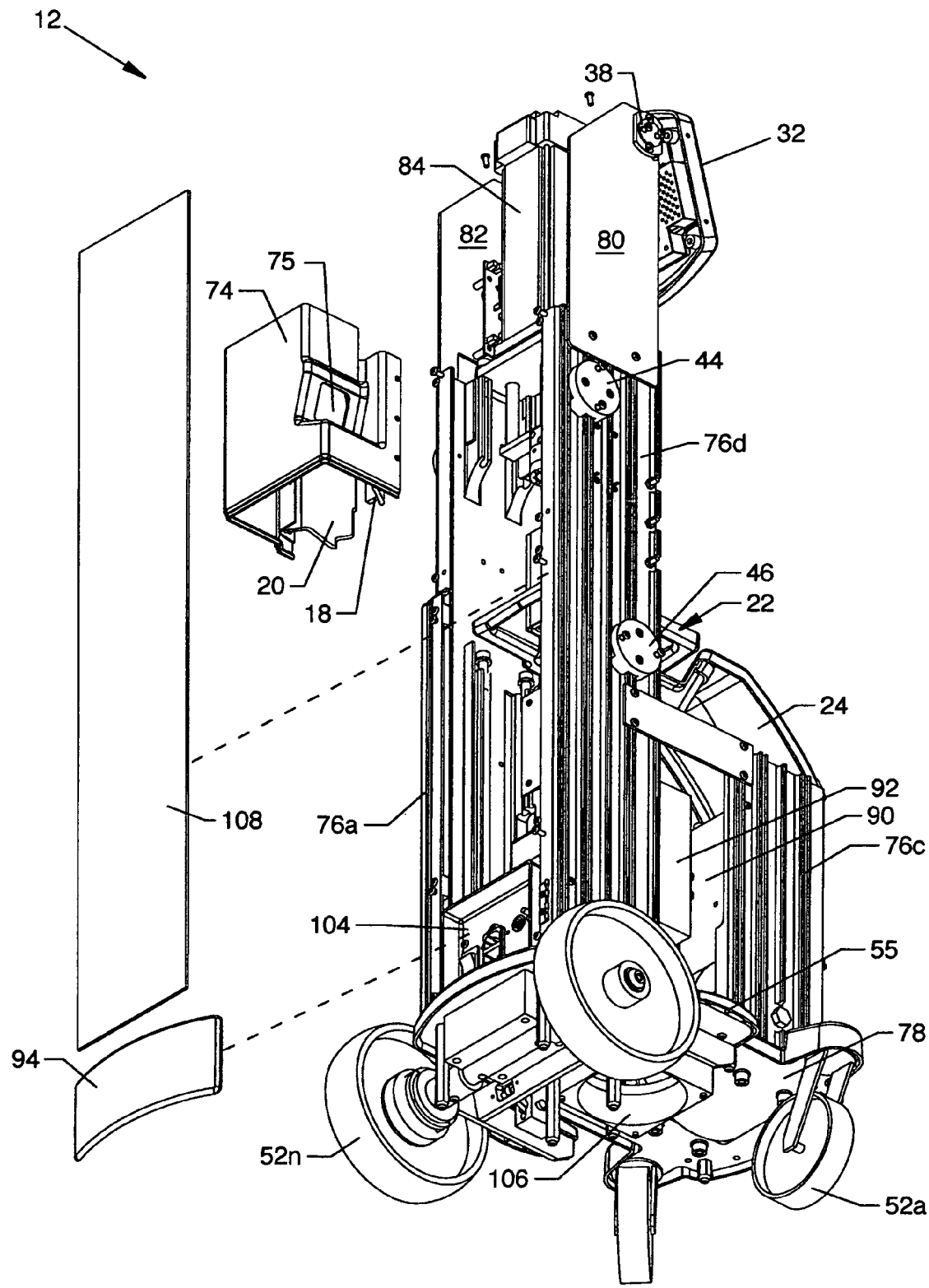
FIG. 4 is a rear view of the drive unit where panels have been removed to reveal components residing in the drive unit.

FIG. 4 is a rear view of the drive unit 12 where the panels 16a-16n have been removed to reveal other components residing in the drive unit 12. The splash guard 74 is shown removed and distanced from the general structure of the drive unit 12. An aperture 75 is included in the splash guard 74 for use with the mirror 87 of the barcode reader assembly 86. The rear access panel 94 is shown removed from the drive unit 12 to reveal the rear connection chassis 104 having a foot switch cord receptacle, a ground plug, a power cord receptacle, and an electrical breaker. A panel 108 is also shown removed from the rear of the drive unit 12. A fan cavity 106 (fan not shown) is located in the base 78 to provide ducted air flow along the interior of the drive unit 12 to cool the reciprocating linear actuator 84 and other components therein. Another internal fan (not shown) is located within the interior of the drive unit 12 to assist with cooling air flow.

Figure 5:
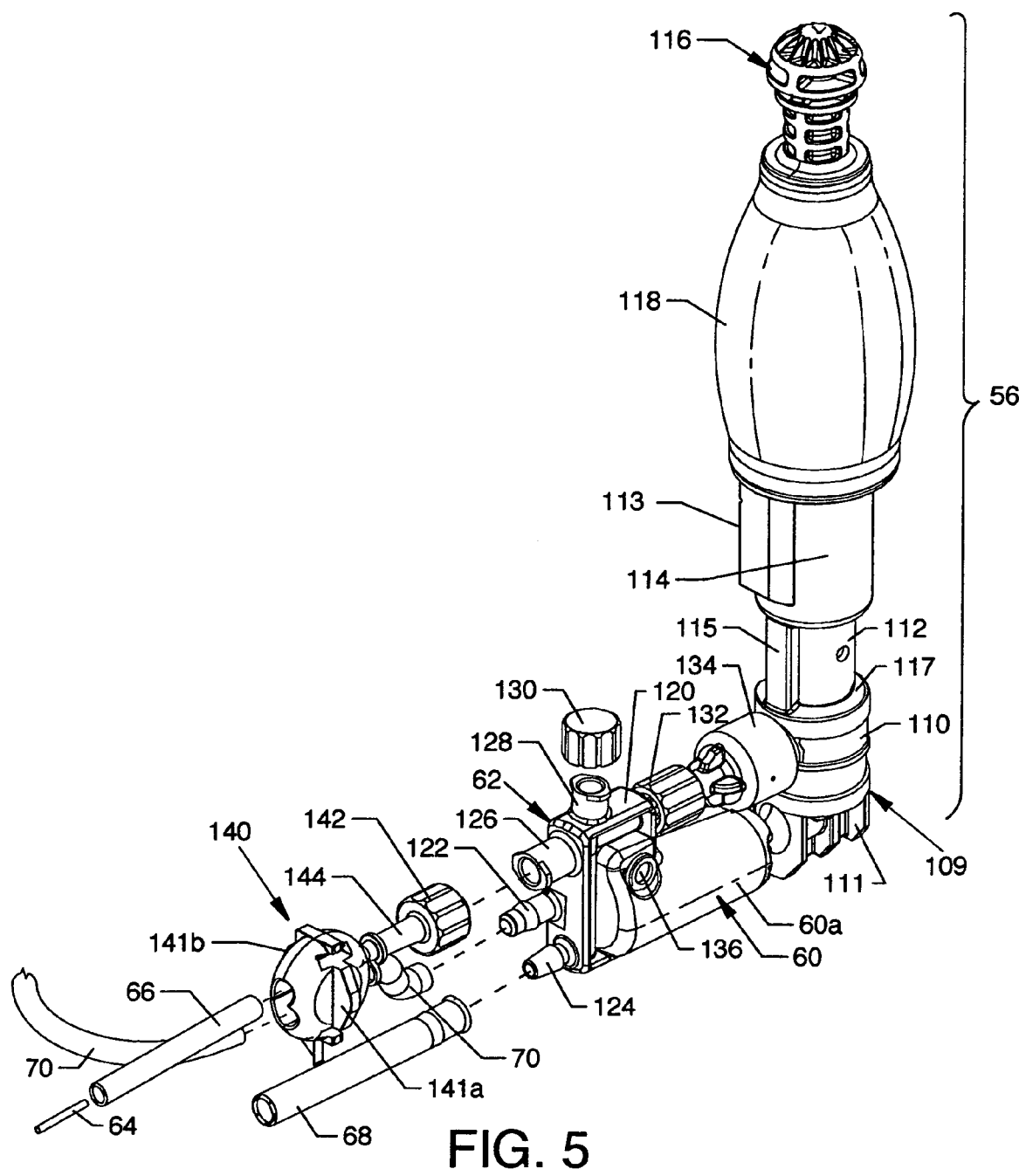
FIG. 5 is an exterior view of the pump, the bubble trap, the connection manifold assembly, and a fixture of the pump/catheter assembly.

FIG. 5 is an exterior view of several components of the pump/catheter assembly 14 generally including the pump 56, the bubble trap 60, the connection manifold assembly 62, and a fixture 140. The pump 56, of generally cylindrical configuration, centers about a tubular body 112 of stainless steel or other suitable material. Components, preferably of impact modified 14% glass nylon, such as ZYTEL® or other suitable plastic, are located about the lower region of the tubular body 112 and include a one-piece base 109 having an upper portion 110 and a continuously formed geometrically configured lower portion 111 both preferably molded continuously about the lower region of the tubular body 112 (FIG. 7). An annular surface 117 is included at the top of the upper portion 110 of the base 109 for intimate contact with capture tabs of the carriage assembly 22 to contain the pump 56 within the carriage assembly 22, as later described in detail. A top body 114, preferably of impact modified 14% glass nylon, such as ZYTEL® or other suitable plastic, is preferably molded continuously about the upper region of the stainless steel tubular body 112. The one-piece base 109 and the top body 114 and a connecting panel 115 are continuously molded or otherwise suitably constructed to encompass the greater part of the tubular body 112. A data plate 113 is also included on the top body 114 for the inclusion of barcode or other informational displays to determine operational parameters of the invention. The pump 56 also includes a hemispherically-shaped pump piston head 116 having configured geometry and a flexible boot 118 connected to and extending between the top body 114 and the pump piston head 116. The geometrically configured lower portion 111 of the base 109 serves as a mount for and is in direct communication with one end of the bubble trap 60, as best viewed in FIGS. 6 and 7. The connection manifold assembly 62 secures directly to the other end of the bubble trap 60 and includes a bracket 120 to which is attached a vertically oriented tubular manifold 148 having a plurality of ports attached therethrough including a saline inlet port 122, an effluent outlet port 124, a Luer style effluent return port 126, and an auxiliary port 128 and cap 130. Also shown are connectors 132 and 134 connectingly extending between the connection manifold assembly 62 and the upper portion 110 of the base 109. The bubble trap 60 includes mating halves 60a and 60b of which mating half 60a is shown. A hydrophobic filter 136 is included at the upper forward region of the bubble trap half 60a. Another hydrophobic filter 138 on the bubble trap half 60b (FIG. 7) opposes the hydrophobic filter 136 on the bubble trap half 60a. The fixture 140, and components associated therewith, assists in support and connection of the effluent return tube 66 to the effluent return port 126 by a connector 142 combined continuously with a connection tube 144, and also assists in support, passage and connection of the saline tube 70 with the saline inlet port 122. The fixture 140 includes outwardly extending vertically aligned and opposed tabs 141a and 141b which prevent the fixture 140 and associated effluent return tube 66 containing the high pressure saline supply tube 64 and the saline supply tube 70 from contacting a roller pump 240 located in the carriage assembly 22, as shown and later discussed in detail.

Figure 6:
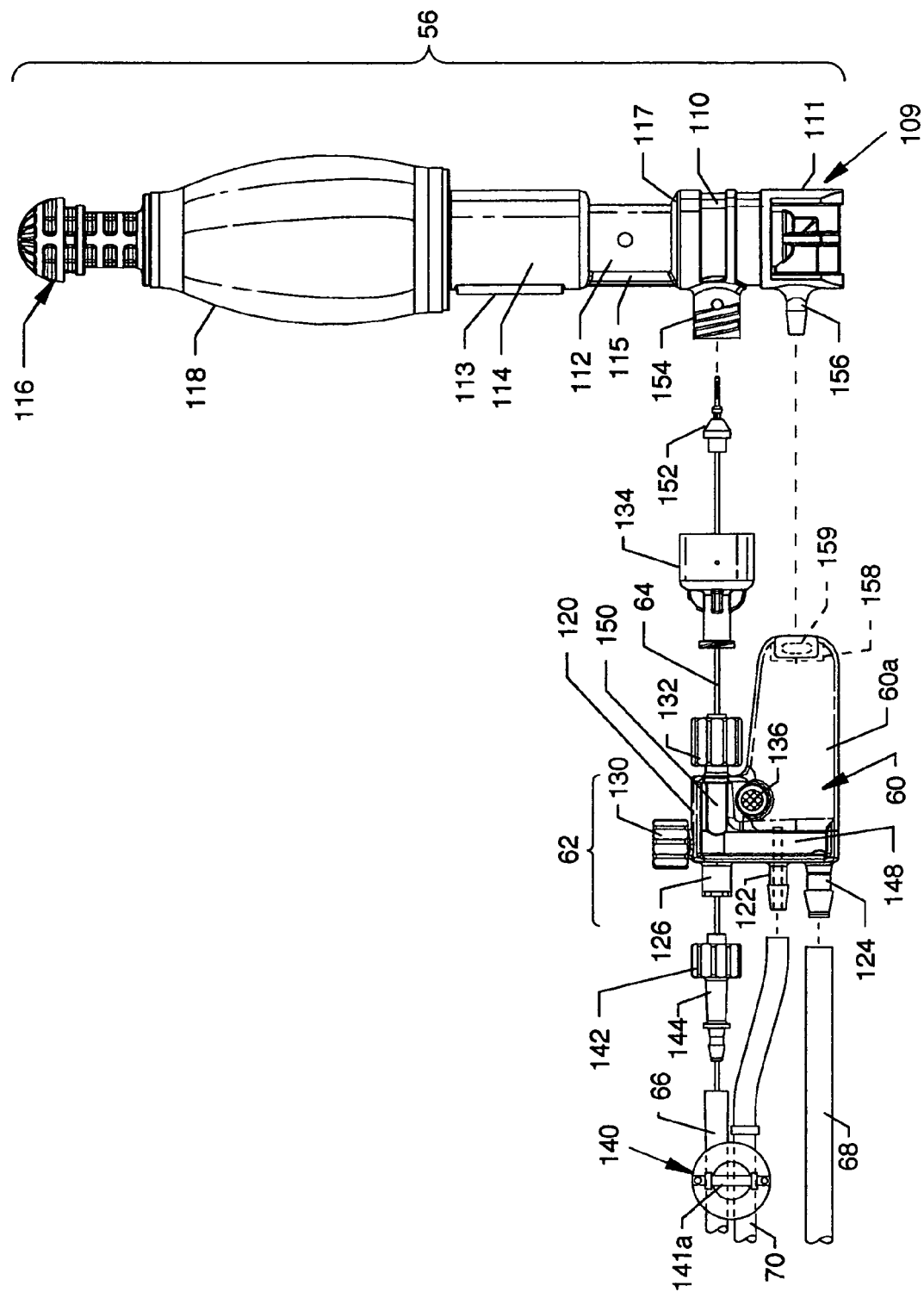
FIG. 6 is a semi-exploded side view of the elements of FIG. 5 illustrating the relationship of the pump, the bubble trap, the connection manifold assembly, and the fixture.
Figure 7:
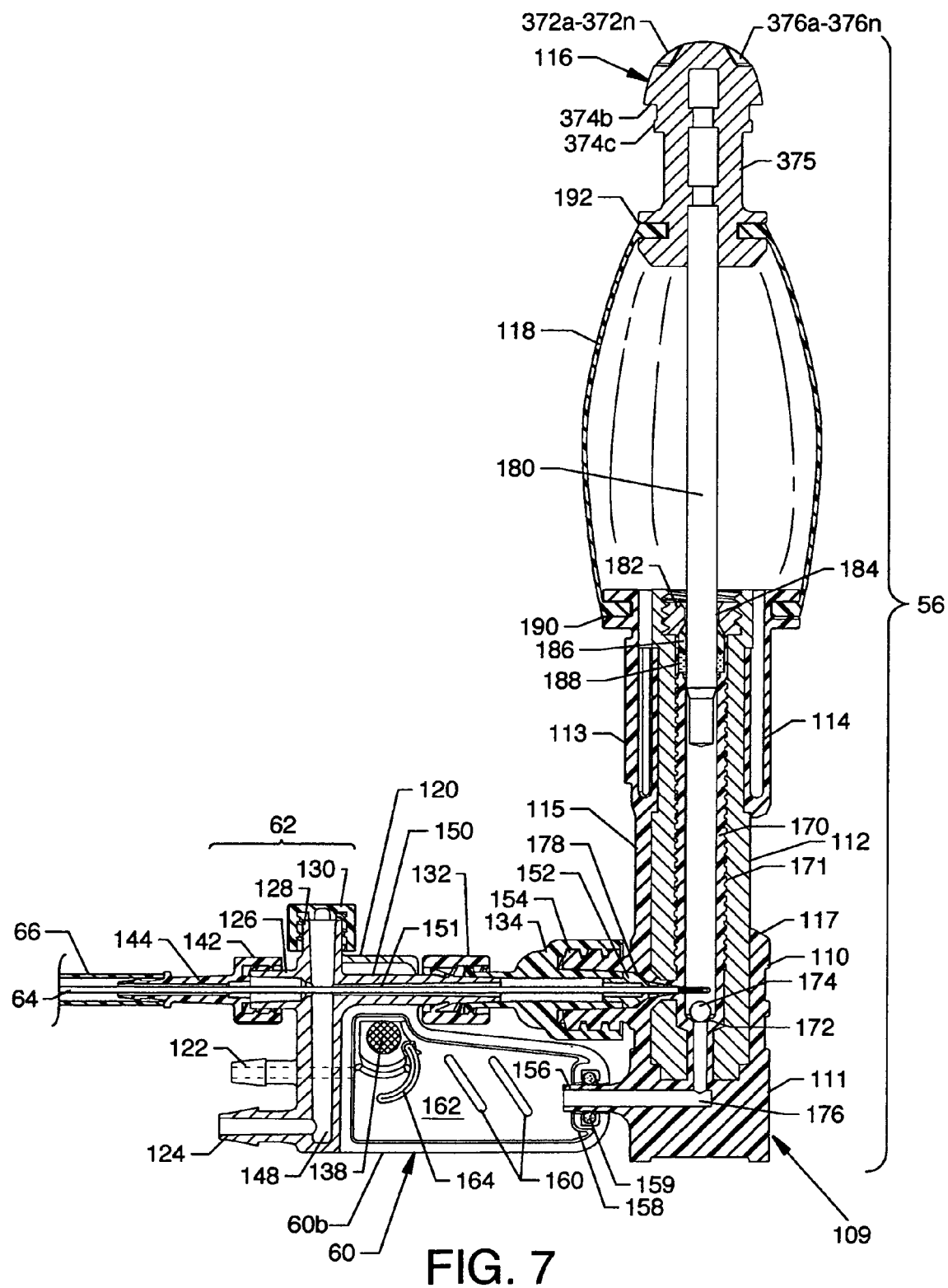
FIG. 7 is a cross section view of the majority of the elements of FIGS. 5 and 6 showing the complete mating of the pump, the bubble trap, and the connection manifold assembly.

FIG. 6 is a semi-exploded side view of the elements of FIG. 5 illustrating the relationship of the pump 56, the bubble trap 60, the connection manifold assembly 62, and the fixture 140. Also shown is the vertically oriented tubular manifold 148 secured to the bracket 120. The effluent outlet port 124 connects to and communicates with the lower interior of the tubular manifold 148. The effluent return port 126 connects to and communicates with the upper interior of the tubular manifold 148. Also connecting to the tubular manifold 148 is a horizontally aligned passage port 150 and closely associated connector 132, each opposing the effluent return port 126. The passage port 150 accommodates the high pressure saline supply tube 64 which extends distally through the lumen 151 (FIG. 7) of the passage port 150, the connector 132, the upper region of the tubular manifold 148, the effluent return port 126, the connector 142, the connection tube 144, and into and through the effluent return tube 66 in coaxial fashion to connect to the thrombectomy catheter 58 (FIG. 1). The proximal end of the high pressure saline supply tube 64 includes a high pressure fitting 152 welded near the distal end of the metal high pressure saline supply tube 64 to facilitate connection of the high pressure saline supply tube 64 for communication with the interior of the pump 56. The proximal end of the high pressure saline supply tube 64, which is the inlet to the high pressure saline supply tube 64, includes a plurality of very small holes (not shown) comprising a filter at the proximal end thereof. The connector 134 has internal and external threads and is aligned over and about the high pressure saline supply tube 64 distal to the high pressure fitting 152 and threadingly engages a threaded connection port 154 extending horizontally from the upper portion 110 of the base 109 of the pump 56. The connector 134 is rotated to intimately engage the high pressure fitting 152 to urge the high pressure fitting 152 into engagement with corresponding mating structure located internally in the pump 56. Connector 132 is utilized to engage the externally threaded end of the connector 134 to secure the connector 134, and thus the pump 56, to the connection manifold assembly 62 and to provide for fixation of the bubble trap 60 to the pump 56. In addition, direct connection and communication between the pump 56 and the bubble trap 60 is provided by a horizontally oriented pump saline inlet port 156 which engages a corresponding geometry receptor port 158 and seal 159 interior to one end of the bubble trap 60. The saline inlet port 122 located on the bracket 120 extends behind the tubular manifold 148 to communicate with the interior of the bubble trap 60 for saline debubbling, whereby unpressurized saline is made available for use by the pump 56.

FIG. 7 is a cross section view of the majority of the elements of FIGS. 5 and 6 showing the complete mating of the pump 56, the bubble trap 60, and the connection manifold assembly 62. Also revealed are one or more transverse obliquely mounted baffles 160 in an interior cavity 162 of the bubble trap half 60b which assist in the direction of, the breakup of, and the dispersion of any ingested bubbles through the saline inlet port 122. An arcuate baffle 164 is located in horizontal alignment with the saline inlet port 122 in order to direct any ingested bubbles upwardly toward the hydrophobic filters 136 and 138. Clearance space is also provided above the baffles 160 and the arcuate baffle 164 allowing upward migration of bubbles along the upwardly sloping top walls of the bubble trap halves 60a and 60b toward the hydrophobic filters 136 and 138 for venting of bubble air overboard.

The pump 56 is an insert molded pump having a tubular body 112 of stainless steel encased in glass-filled impact modified nylon, such as ZYTEL® or other suitable material, to provide structural integrity for the pump 56. Glass-filled impact modified nylon is continuously molded on both the inside and outside of the tubular body 112 to provide high tolerance features making the pump 56 much more economical to produce and more reproducible. Glass-filled impact modified nylon is incorporated for use in the upper portion 110 and the geometrically configured lower portion 111 of the base 109, and in the top body 114, and is molded continuously about the tubular body 112. Also, it is incorporated into use as a centrally located cylinder 170 molded to the cylindrical-like inner wall 171 of the tubular body 112. A check ball seat 172 located in the lower region of the cylinder 170 is part of the continuously molded glass-filled impact modified nylon and accommodates a large stainless steel inlet check ball 174. The check ball seat 172 is molded to best accommodate the inlet check ball 174 for proper sealing during the pressurization stroke of a pump piston 180. The check ball seat 172 is supported underneath by the lower portion of the tubular body 112. This arrangement provides dissimilar materials for the sealing arrangement. The mutual contacting of the stainless steel inlet check ball 174 and the molded glass-filled impact modified nylon of the check ball seat 172 gives sufficient compliance to ensure a reliable seal. A passage 176 extends from the check ball seat 172 and through the pump saline inlet port 156. Mating structure conforming to the shape of the high pressure fitting 152 in the form of a configured receptor 178 is located in the molded glass-filled impact modified nylon of the upper portion 110 of the base 109 intersecting the interior of the cylinder 170 just above the check ball seat 172. The piston 180 engages the interior of the cylinder 170 to interact therein to provide for intake of saline during upstroke movement and for pressurization of saline during downstroke movement in concert with the positioning of the inlet check ball 174. Provision for sealing the piston 180 with the cylinder 170 is also provided. A stainless steel threaded insert 182 with a centrally located body hole 184 engages an internal thread at the upper end of the tubular body 112 to forcibly retain a cylindrically-shaped open end high pressure seal 186 of UHMWPE (ultra high molecular weight polyethylene) or HDPE (high density polyethylene) against the upper region of the cylinder 170 where the high pressure seal 186 seals against the piston 180. A silicone O-ring 188 is located between the bottom of the high pressure seal 186 and the top of the cylinder 170. The flexible boot 118 extends between and attaches between an annular boot mounting groove 190 at the top of the top body 114 and an annular boot mounting groove 192 at the lower region of the pump piston head 116.

Figure 8:
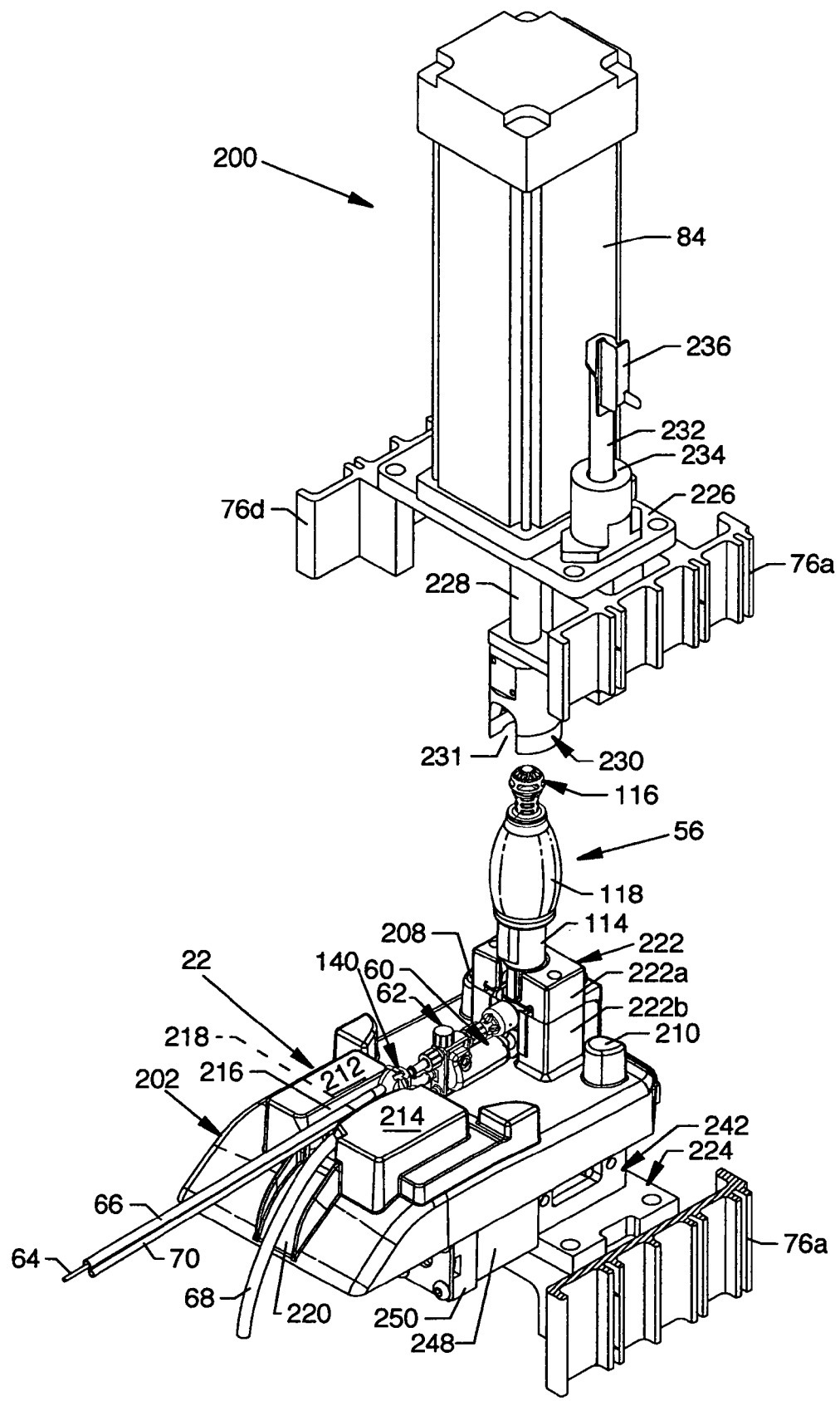
FIG. 8 is a view showing components which locate centrally in the instant invention and which are of major significance to the operation of the instant invention, including a carriage assembly, a pump aligned within and capturing components of the carriage assembly, and a linear actuator assembly in alignment to specific regions of the carriage assembly and to the pump.

FIG. 8 is a view showing components which locate centrally in the instant invention and which are of major significance to the operation of the instant invention. Shown are the carriage assembly 22, the pump 56 aligned within and capturing components of the carriage assembly 22, and a linear actuator assembly 200 in alignment to specific regions of the carriage assembly 22 and to the pump 56. A cover 202, having a configured shape and multiple features, aligns over and about the mechanism structure incorporated to operate the carriage assembly 22. Features of the cover 202 are also included to prevent contact of the effluent return tube 66 and contained high pressure saline supply tube 64 and the saline supply tube 70, which are captively held by the fixture 140, with a roller pump 240.

Figures 9, 10A, 10B, 10C:
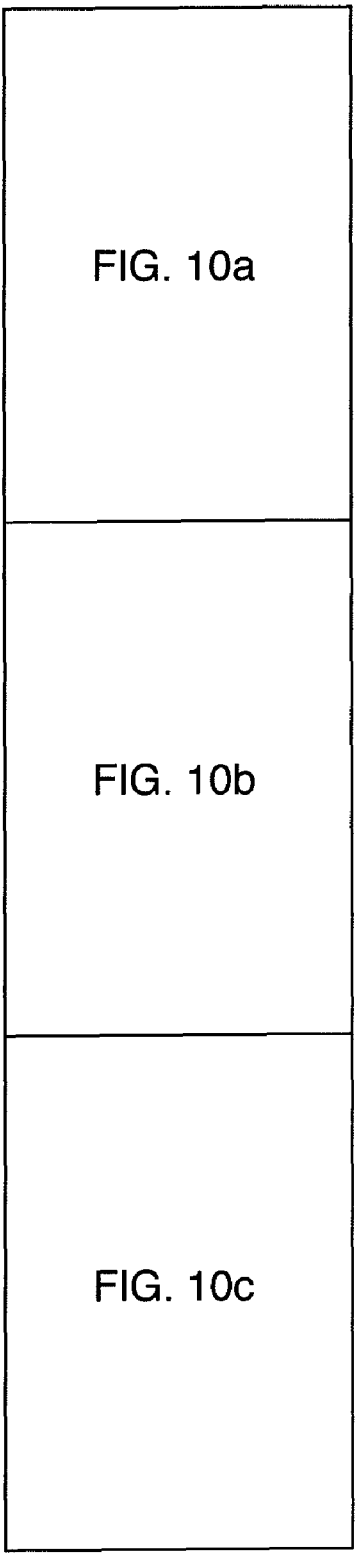
FIG. 9 illustrates the alignment of FIGS. 10a and 10b with respect to each other.
FIGS. 10a and 10b combine to show an exploded isometric view of the components comprising the carriage assembly, and FIG. 10c references the relationship of a pivotable top mounting plate to a configured bracket and a load cell.
Figure 10A:
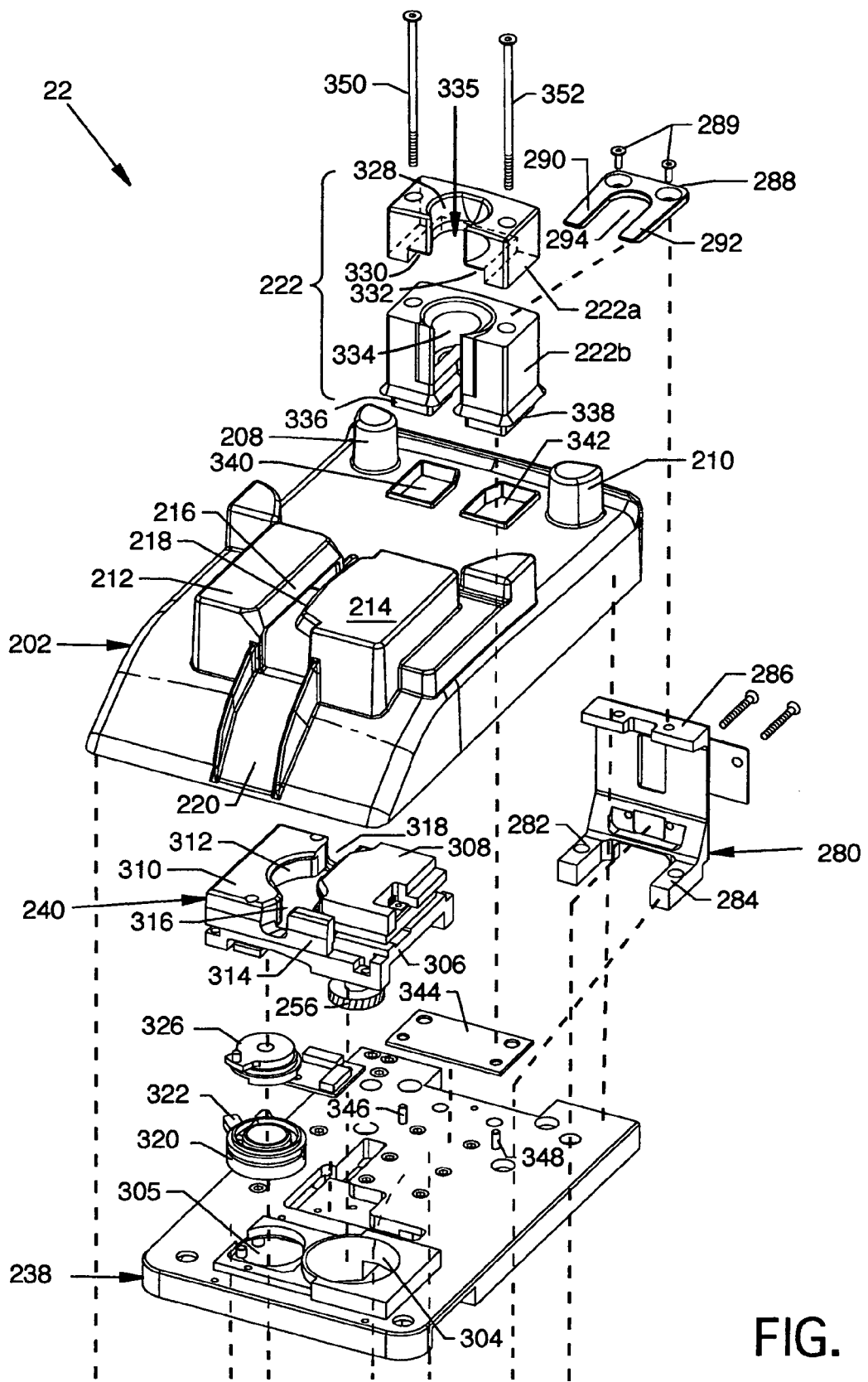
Figure 10B:
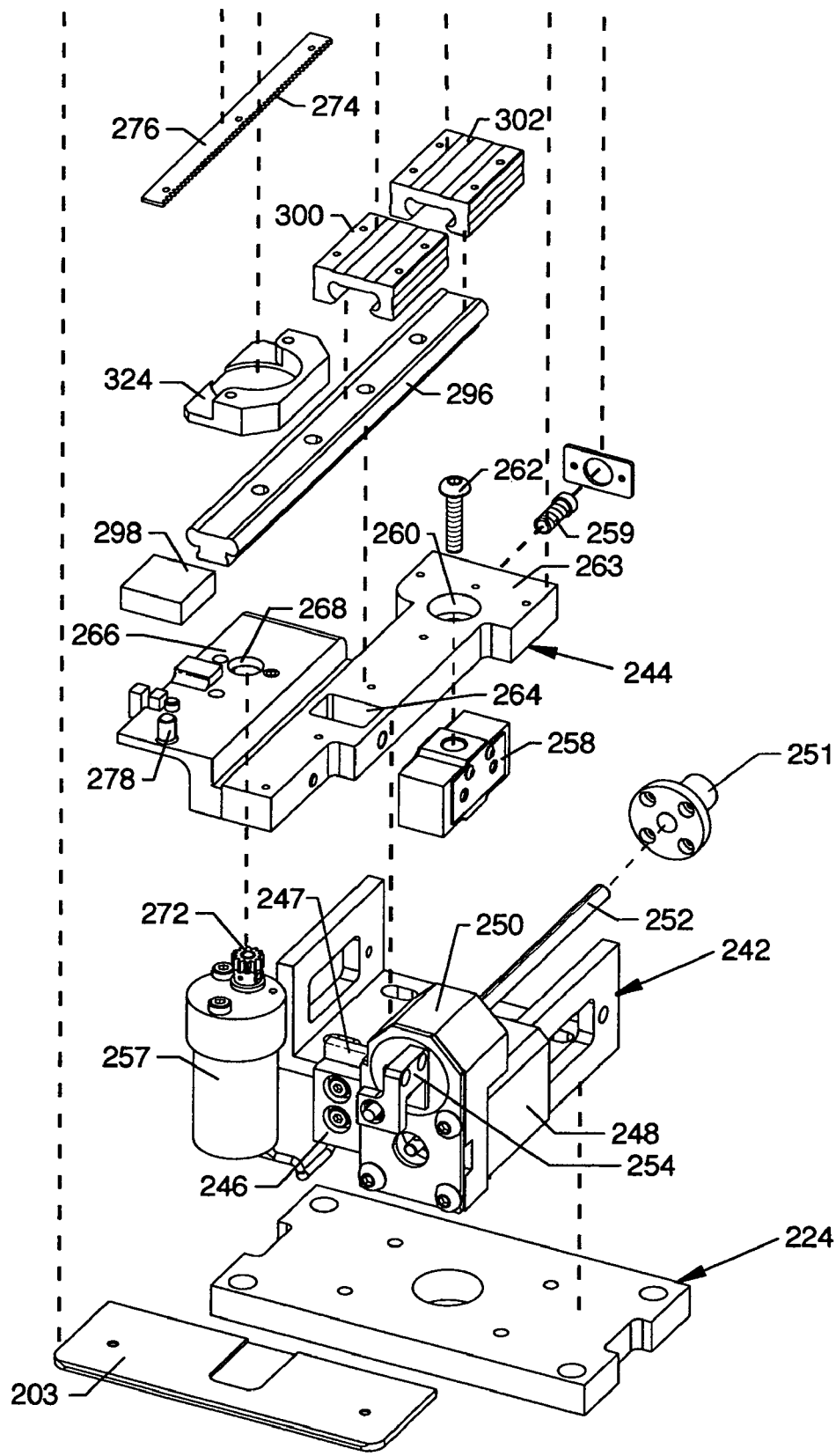
Figure 10C:
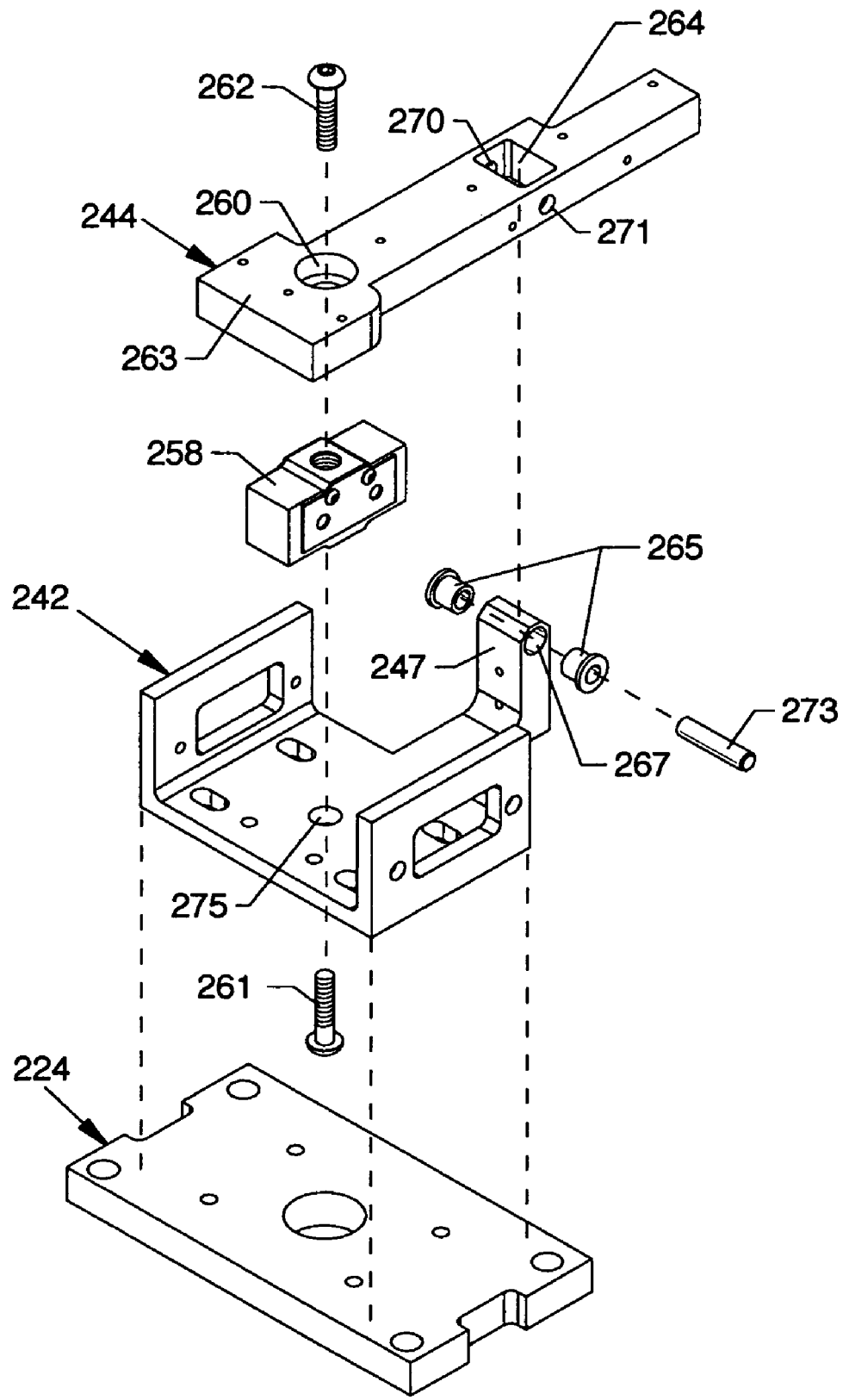
Figure 25:
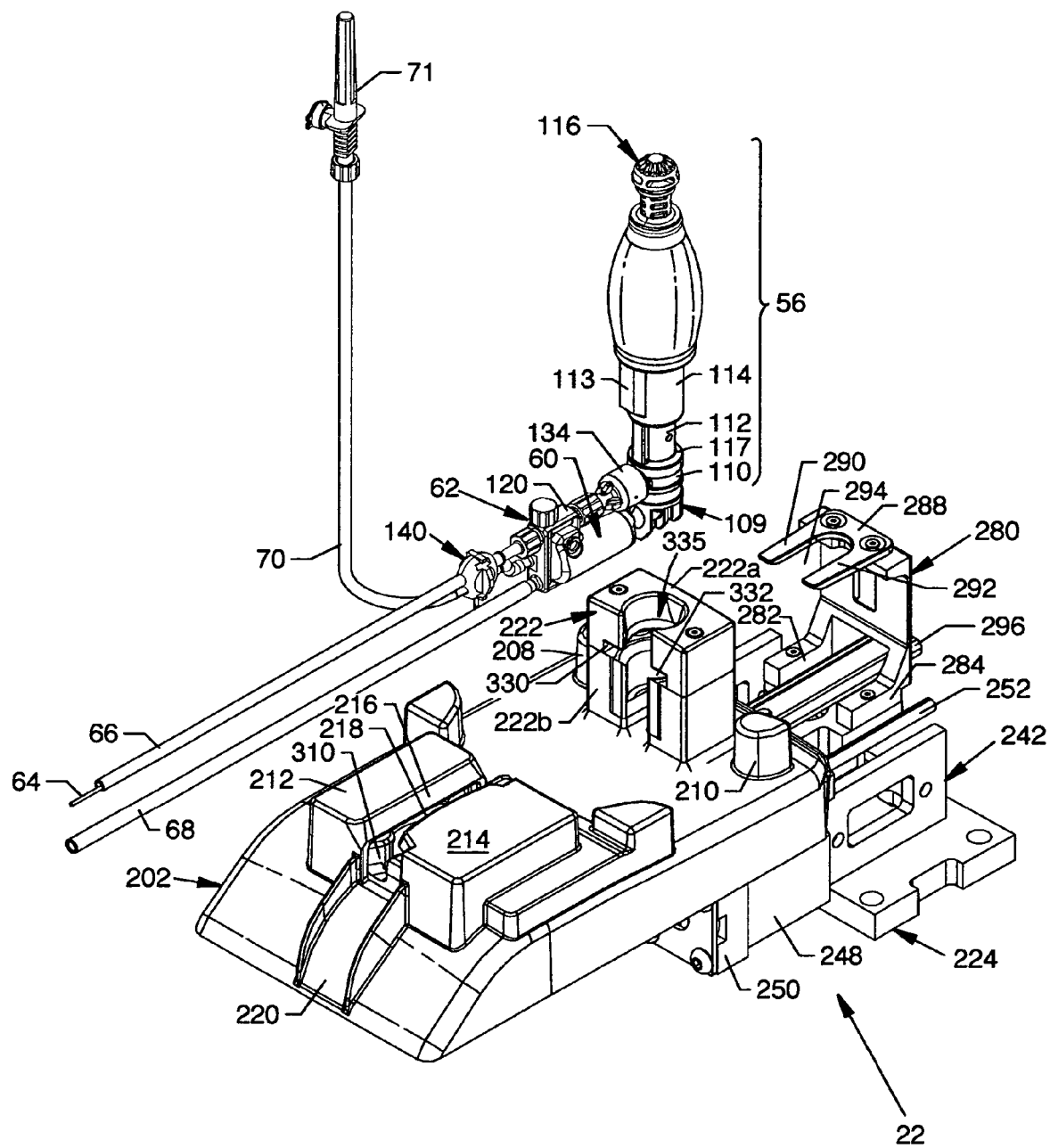
FIG. 25 is an isometric view of the pump prior to insertion into and accommodation by the capture block of the carriage assembly; and, FIG. 26 is a barcode flow chart.

Opposed cams 208 and 210 extend upwardly from the top surface of the cover 202 to open the normally closed doors 18 and 20 which are pivotally operated about living hinges at the forward region of the splash guard 74. Also extending upwardly from the top surface and near the front of the cover 202 are opposed tube guides 212 and 214, generally being rectangular and box-like in shape, but including opposed angled surfaces 216 and 218 which direct the effluent return tube 66 for engagement with a roller pump and other associated structure underlying the opposed tube guides 212 and 214 during loading. The tube guides 212 and 214 also function as covers for components of the roller pump 240 which are located directly beneath. The opposed angled surfaces 216 and 218 can also contact the tabs 141a and 141b of the fixture 140 to prevent entry of the associated effluent return tube 66 containing the high pressure saline supply tube 64 and the saline supply tube 70 from contacting the roller pump 240 located in the carriage assembly 22. The opposed angled surfaces 216 and 218 are also shown in FIG. 10a and FIG. 25. A channel 220 is also included at the front of the cover 202 for accommodation of the effluent waste tube 68. A two-piece capture block 222 having configured geometry is comprised of a capture block top 222a and a capture block bottom 222b, the bottom portion of the latter being aligned to the upper surface of the cover 202 and secured to other underlying structure, as described later in detail. The capture block 222 provides and coordinates alignment of the upper portion 110 and the geometrically configured lower portion 111 of the base 109 of the pump 56 to the carriage assembly 22. Other components assist to secure the pump 56 in the capture block 222, as described later in detail. A horizontally oriented bottom mounting plate 224, a part of the carriage assembly 22, secures between the support structures 76a and 76d. Also mounted between the support structures 76a and 76d, but at a higher level, is the mounting plate 226 associated with the linear actuator assembly 200. The reciprocating linear actuator 84 secures to the mounting plate 226 and includes an actuator shaft 228 freely extending through the mounting plate 226 and a cylindrically-shaped pump connector 230 secured to the bottom of the actuator shaft 228. Downward actuation of the actuator shaft 228 causes automatic and secure overhead snap engagement of the pump connector 230 with the pump piston head 116 of the pump 56 for subsequent reciprocating operation of the pump 56. Disengagement of the pump connector 230 from the piston pump head 116 is automatic when the carriage assembly 22 is operated to the extended open position where the pump piston head 116 exits the pump connector 230 through a side opening 231. The pump connector 230 is described later in detail. A stroke limit shaft 232, a stroke limit shaft mount 234, and a stop fixture 236 on the upper portion of the stroke limit shaft 232 are also shown.

FIG. 9 illustrates the alignment of FIGS. 10a and 10b with respect to each other.

FIGS. 10a and 10b combine to show an exploded isometric view of the components comprising the carriage assembly 22. FIG. 10c is an exploded rear view referencing pivotal mounting of a top mounting plate 244 to a configured bracket 242 and a load cell 258 secured therebetween.

Figure 11:
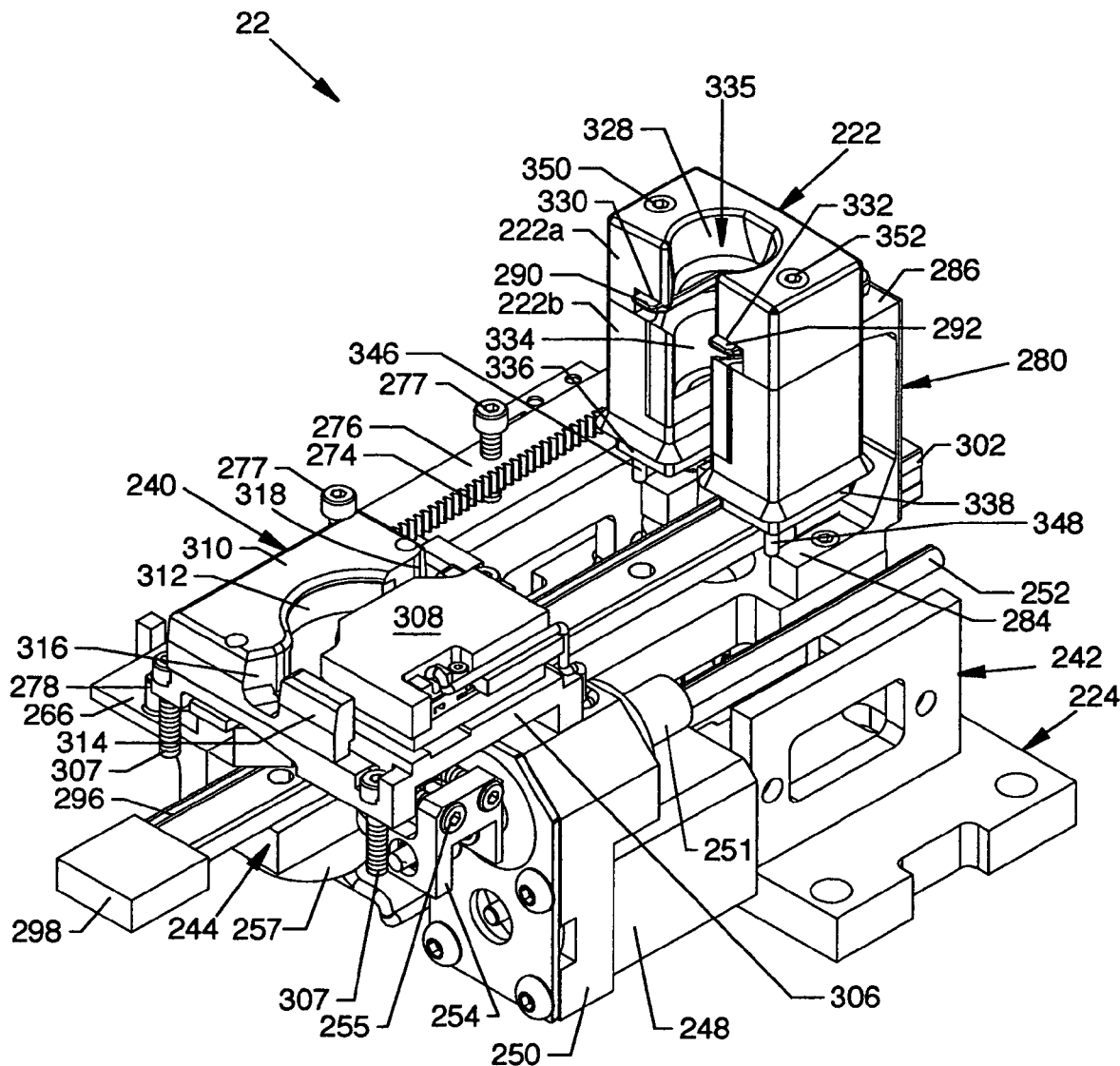
FIG. 11 is a right side top view of the carriage assembly.
Figure 12:
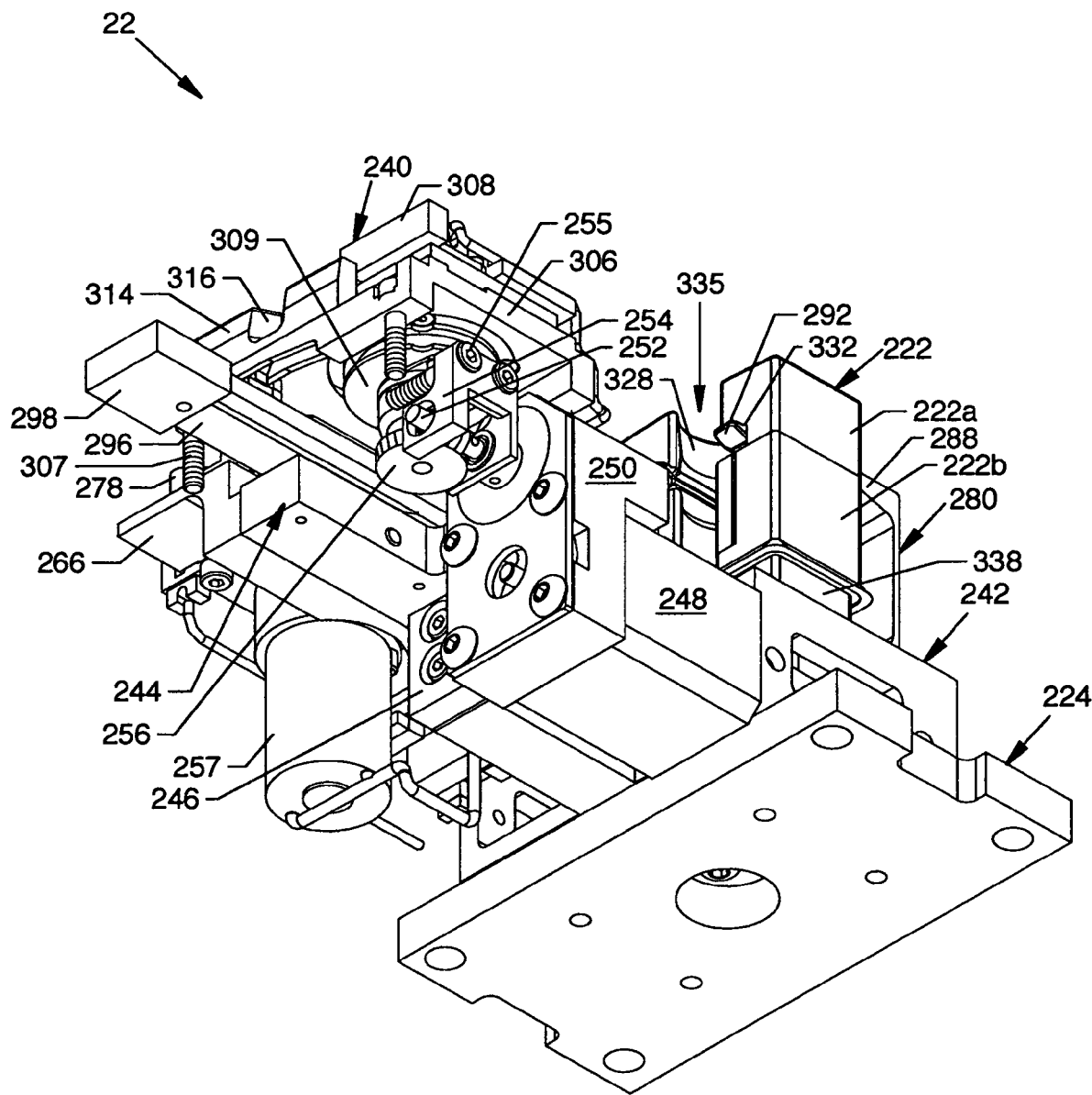
FIG. 12 is a right side bottom view of the carriage assembly.
Figure 13:
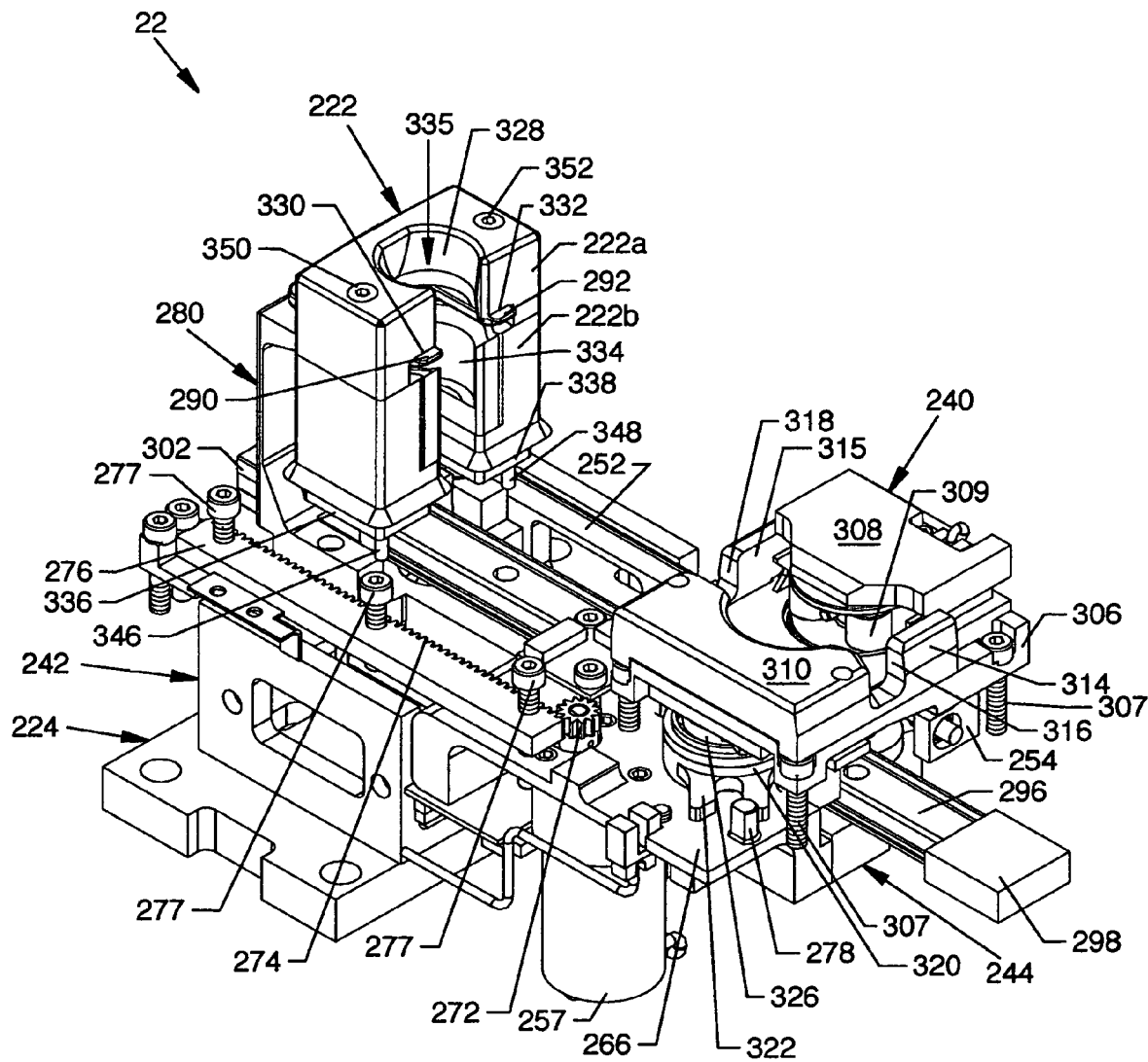
FIG. 13 is a left side top view of the carriage assembly.
Figure 14:
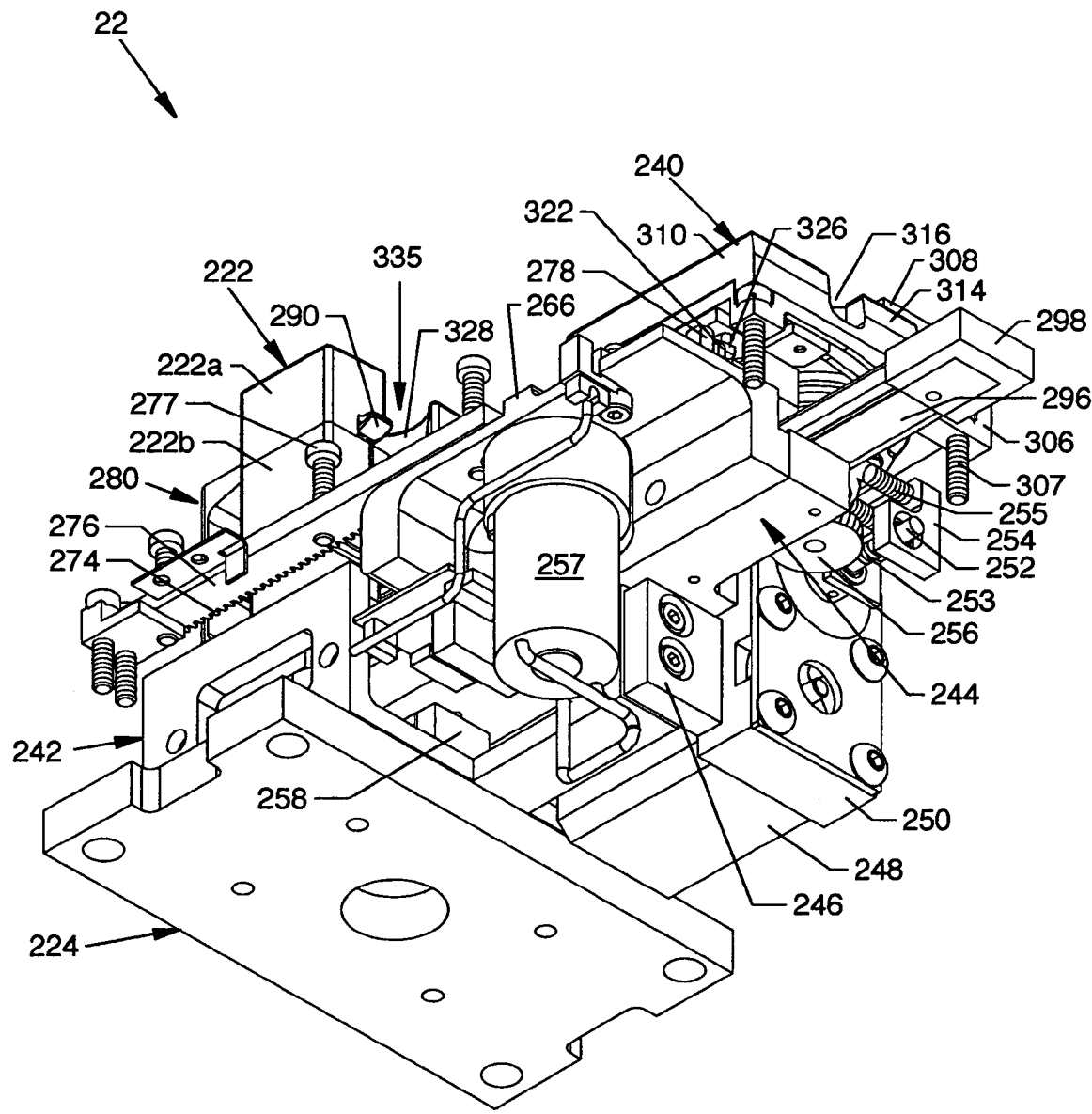
FIG. 14 is a left side bottom view of the carriage assembly.

FIG. 11 is a right side top view of the carriage assembly 22, FIG. 12 is a right side bottom view of the carriage assembly 22, FIG. 13 is a left side top view of the carriage assembly 22, and FIG. 14 is a left side bottom view of the carriage assembly 22. For purposes of brevity and clarity, the cover 202, the carriage plate 238, and the front truck 300 are not shown in FIGS. 11, 12, 13 and 14.

With reference to FIGS. 10a, 10b, 10c, 11, 12, 13 and 14, the carriage assembly 22 is now described. The carriage assembly 22 includes components which are stationary and components which are movably actuated with respect to the stationary components to a closed or open position during operation of the carriage assembly 22. The interaction of the stationary components with the movably actuated components to the closed position provides for capturing and transporting the pump 56 for automatic coupling to and actuation by the linear actuator assembly 200, as well as simultaneously accomplishing interfacing of the effluent waste tube 68 with the roller pump 240 and, when the procedure is finished, provides simultaneous interaction in the reverse order to the open position to provide automatical decoupling of the pump 56 from the linear actuator assembly 200 and for disengagement of the effluent waste tube 68 from the roller pump 240.

Some substantial mounting structure components which are generally stationary and connected include the bottom mounting plate 224, the configured bracket 242 which suitably and adjustably secures to the top of the bottom mounting plate 224. Other structure generally being stationary suitably aligns and secures to the above mentioned substantial mounting structure components including a mounting flange 246 secured to the side of a vertically oriented pivot flange 247 at the front of the configured bracket 242 to accommodate a roller pump motor 248 and a gear drive 250 which is coupled to a roller pump motor 248. A pivotable top mounting plate 244, a substantial mounting structure, secures in pivotal fashion to the vertically oriented pivot flange 247 which extends vertically from the forward region of the configured bracket 242. A pinion shaft 252, which is slotted, slidingly engages the gear drive 250. The near end of the pinion shaft 252 is machined to include mounting of a pinion gear 253 (FIG. 14) and is rotatingly captured in a pinion shaft end bracket 254. A pinion shaft support 251 aligns over and about the pinion shaft 252 and secures to the rear of the gear drive 250. The pinion shaft end bracket 254 secures to the underside of the positionable carriage plate 238 with a plurality of screws 255 (FIG. 11) and maintains contact of the pinion gear 253 at the near end of the pinion shaft 252 with a roller pump drive gear 256 extending perpendicularly from the roller pump 240. As the carriage plate 238 and attached components are movably actuated by the action of a carriage motor 257, as later described in detail, the attached pinion shaft end bracket 254 slidingly repositions the connected pinion shaft 252 within the gear drive 250. Rotational force can be delivered by the pinion shaft 252 to the movably actuated roller pump 240 regardless of the horizontal position of the roller pump 240 with respect to roller pump motor 248. An aperture 264 is included extending through the top mounting plate 244 to pivotally accommodate the upper portion of the pivot flange 247 extending vertically from the configured bracket 242. Opposed pivot bushings 265 align in a horizontally aligned bore 267 at the upper portion of the pivot flange 247. The bore 267 and the included pivot bushings 265 align within the aperture 264 and with horizontally aligned and opposed holes 270 and 271 adjacent to the aperture 204 and are pivotally secured therein by a pin 273 extending coaxially through the pivot bushings 265, the bore 267, and the holes 270 and 271 thereby pivotally securing the upper end of the pivot flange 247 within the aperture 264. Thus, a portion of the top mounting plate 244 is supported in pivotal fashion and the top mounting plate 244 and components secured directly thereto can pivot a short distance thereabout. Such pivotal action is useful in sensing the force applied to the pump 56 by the reciprocating linear actuator 84. Additional attachment by use of the load cell 258 of the top mounting plate 244 to the bottom mounting plate 224 is provided by a screw 262 extending through a recessed hole 260 in the top mounting plate 244, and into the top of the load cell 258, and by another screw 261 extending through a hole 275 in the bottom of the configured bracket 242 into the bottom of the load cell 258. Downward force delivered to the pump 56 by the reciprocating linear actuator 84 is sensed by force transmitted through the capture block 222, the slides 300 and 302, the linear guide 296, and the top mounting plate 244 to apply varied forces to the load cell 258.

A horizontally aligned adjustable stop 259 is included in threaded engagement with the rear edge of the top mounting plate 244 to impinge an internally mounted pressure sensor (not shown) to facilitate alignment of the capture block 222 with the linear actuator assembly 200, more specifically, with the pump connector 230 and to signal closure of the carriage plate 238. A carriage motor mounting plate 266 secures to one edge of the top mounting plate 244 and includes an aperture 268. The carriage motor 257, which includes a gear 272, suitably secures to the underside of the carriage motor mounting plate 266, with the gear 272 aligning to and extending through and above the aperture 268 to engage a plurality of teeth 274 of a linear guide 276 which is secured to the underside of the carriage plate 238 by a plurality of screws 277 (FIG. 11). Such a relationship provides for power to movably actuate the carriage plate 238 and associated components, as later described in detail. A cam post 278 extends perpendicularly from the carriage motor mounting plate 266 for interaction with components closely associated with the roller pump 240, as later described in detail, including a cam assembly 320. The top mounting plate 244 includes a rearwardly located wide portion 263 for suitable mounting of a capture clip mounting bracket 280. The capture clip mounting bracket 280 includes opposed and spaced horizontally oriented feet 282 and 284 which mate to the rearwardly located wide portion 263 of the top mounting plate 244. A top plate 286 of the capture clip mounting bracket 280 accommodates a horizontally oriented capture clip 288 which suitably secures thereto, as by fasteners 289. The capture clip 288 includes opposed beveled end capture tabs 290 and 292 spaced by a slot 294. The capture clip 288 is instrumental in automatic securing of the pump 56 to the carriage assembly 22. A linear guide 296 having a "T" cross section suitably secures to the upper surface of the top mounting plate 244. A stop block 298 secures to the near end of the linear guide 296.

Movably actuated components of the carriage assembly 22 include the carriage plate 238 and other attached components, as now described. Direct positionable coupling of the carriage plate 238 to the linear guide 296 is provided by a front truck 300 and a similarly constructed rear truck 302 which suitably mount to the underside of the carriage plate 238 and which slidingly engage the linear guide 296. One end of the carriage plate 238 includes features for mounting of other components, such features including a circular opening 304 for accommodation of structure of the roller pump 240, and a cam assembly cavity 305. The roller pump 240 aligns to and suitably secures to the upper side of the carriage plate 238 with the roller pump drive gear 256 aligning to and extending through the opening 304. The roller pump 240 includes a base 306 secured to the carriage plate 238 by a plurality of screws 307 (FIG. 11), a roller cover 308 mounted to the base 306 which houses a roller assembly 309 (FIG. 13), a positionable outside race or platen 310 having an interior arcuate surface 312 and being positionable across and along the base 306, a front guide 314 and a mirror image-like rear guide 315 (FIG. 13), and opposed front and rear receptor slots 316 and 318 in the front guide 314 and the rear guide 315, respectively, adjacent to the arcuate surface 312. A cam assembly 320 having a slotted tab 322 extending horizontally therefrom secures to the upper region of the carriage plate 238 utilizing the cam assembly cavity 305 and a cam assembly mount 324. The cam assembly 320 is located just below and in close communication with the positionable outside race or platen 310 of the roller pump 240, whereby the position of the positionable outside race or platen 310 is influenced by the slotted cam 322. The slotted cam 322 can engage the cam post 278 extending from the carriage motor mounting plate 266 to facilitate positioning of the positionable outside race or platen 310 toward or away from the pump roller assembly 309 under the roller cover 308 in cooperation with a rotating cam post assembly 326 located between the cam assembly 320 and the outside race or platen 310 to automatically engage or disengage the effluent waste tube 68. A position encoder (not shown) is located on the underside of the roller pump 240 in close alignment with and above the roller pump gear 256 to verify the rotational speed of the roller pump 240.

The two-piece capture block 222 having configured geometry is comprised of a capture block top 222a and a capture block bottom 222b. A vertically aligned arcuate surface 328 is located in the capture block top 222a intersecting opposed partially formed rectangular-shaped slots 330 and 332 located on the underside of the capture block top 222a. The capture block bottom 222b includes a vertically aligned arcuate surface 334. The top of the capture block bottom 222b engages the bottom of the capture block top 222a to complete the formation of the rectangular-shaped slots 330 and 332 which extend horizontally from the front to the back of the assembled capture block 222 and to aligningly combine the arcuate surface 328 of the capture block top 222a with the arcuate surface 334 of the capture block bottom 222b to form a continuous receptor slot 335 (FIG. 11) which is utilized to accommodate loading of the pump 56. The capture tabs 290 and 292 of the capture clip 288 extend fully through the slots 330 and 332 when the carriage assembly 22 is movably actuated to the closed position to engage the geometry of and capture the pump 56 when located within the receptor slot 335 formed by the arcuate surfaces 328 and 334 of the capture block 222. The capture block bottom 222b includes a left and right skirted base 336 and 338, respectively, which engage apertures 340 and 342 at the rear top portion of the cover 202. The bottoms of the left skirted base 336 and the right skirted base 338 extend through the apertures 340 and 342 to rest and secure against a spacer plate 344 which, in turn, aligns to the top surface of the carriage plate 238. Vertically oriented alignment pins 346 and 348 secure in the carriage plate 238 and extend upwardly through holes in the spacer plate 344 into holes (not shown) in the bottoms of the left skirted base 336 and the right skirted base 338. Fastener screws 350 and 352 extend through vertically aligned holes in the capture block top 222a, the capture block bottom 222b, holes in the spacer plate 344, and into threaded holes in the carriage plate 238 to secure the capture block 222 to the carriage plate 238. A bottom cover 203 mates to the underside of the cover 202.

Figure 15:
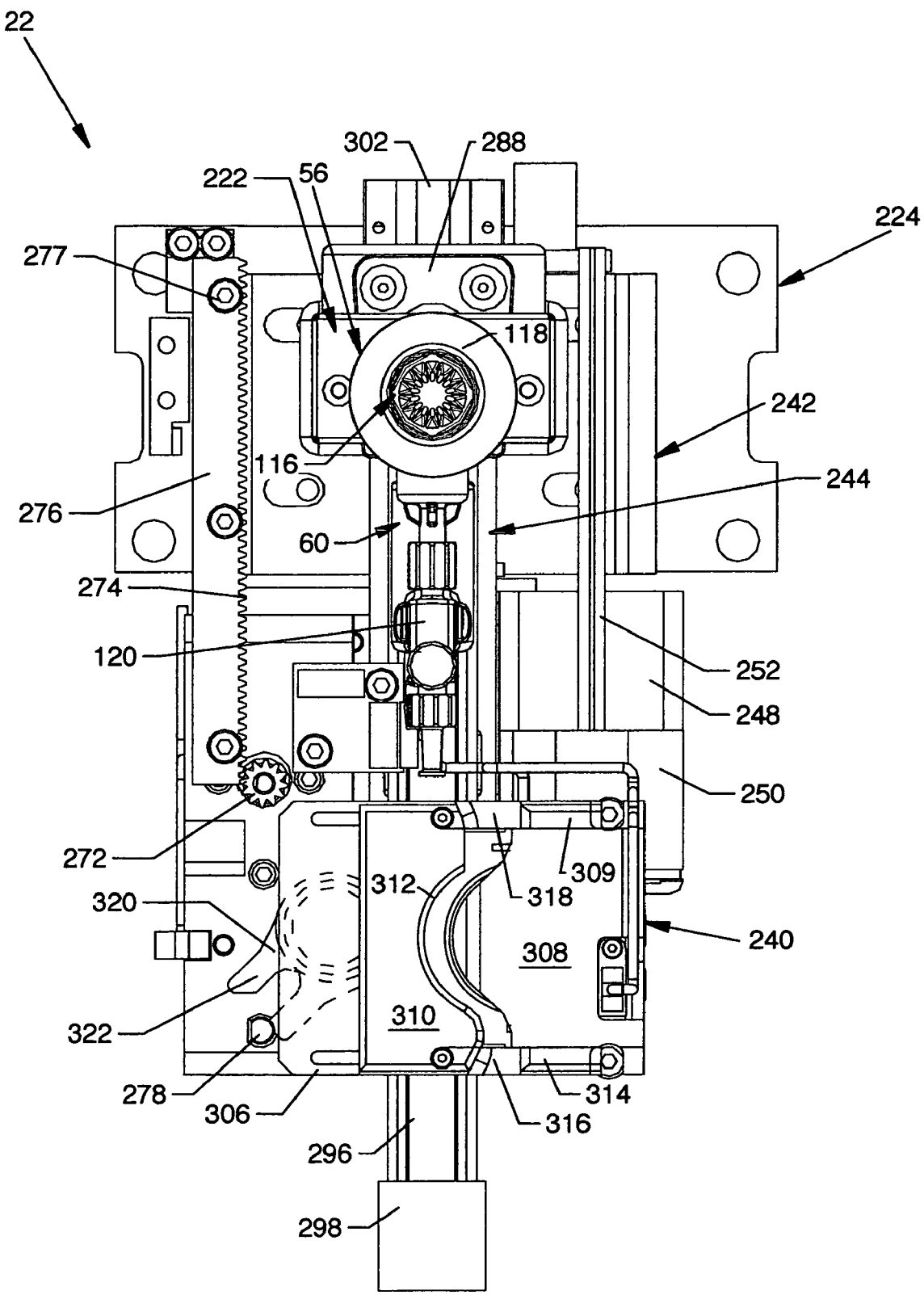
FIG. 15 is a top view of the carriage assembly where the cover and the carriage plate have been removed.

FIG. 15 is a top view of the carriage assembly 22 where the cover 202 and the carriage plate 238 have been removed for the purposes of brevity and clarity. The pump 56 is shown capturingly engaged within the capture block 222. The positionable tube clamp 310 of the roller pump 240 is shown actuated to the closed position as a result of interaction of the slotted tab 322 of the cam assembly 320 with the cam post 278 during inward positioning of the carriage plate 238 to the closed position in order to automatically capture the effluent waste tube 68 (FIG. 8) between the arcuate surface 312 of the positionable tube clamp 310 and the roller assembly 309 located beneath roller cover 308. Outward positioning of the carriage plate 238 to the open position releases the effluent waste tube 68 from influence of the roller pump 240.

Figure 16:
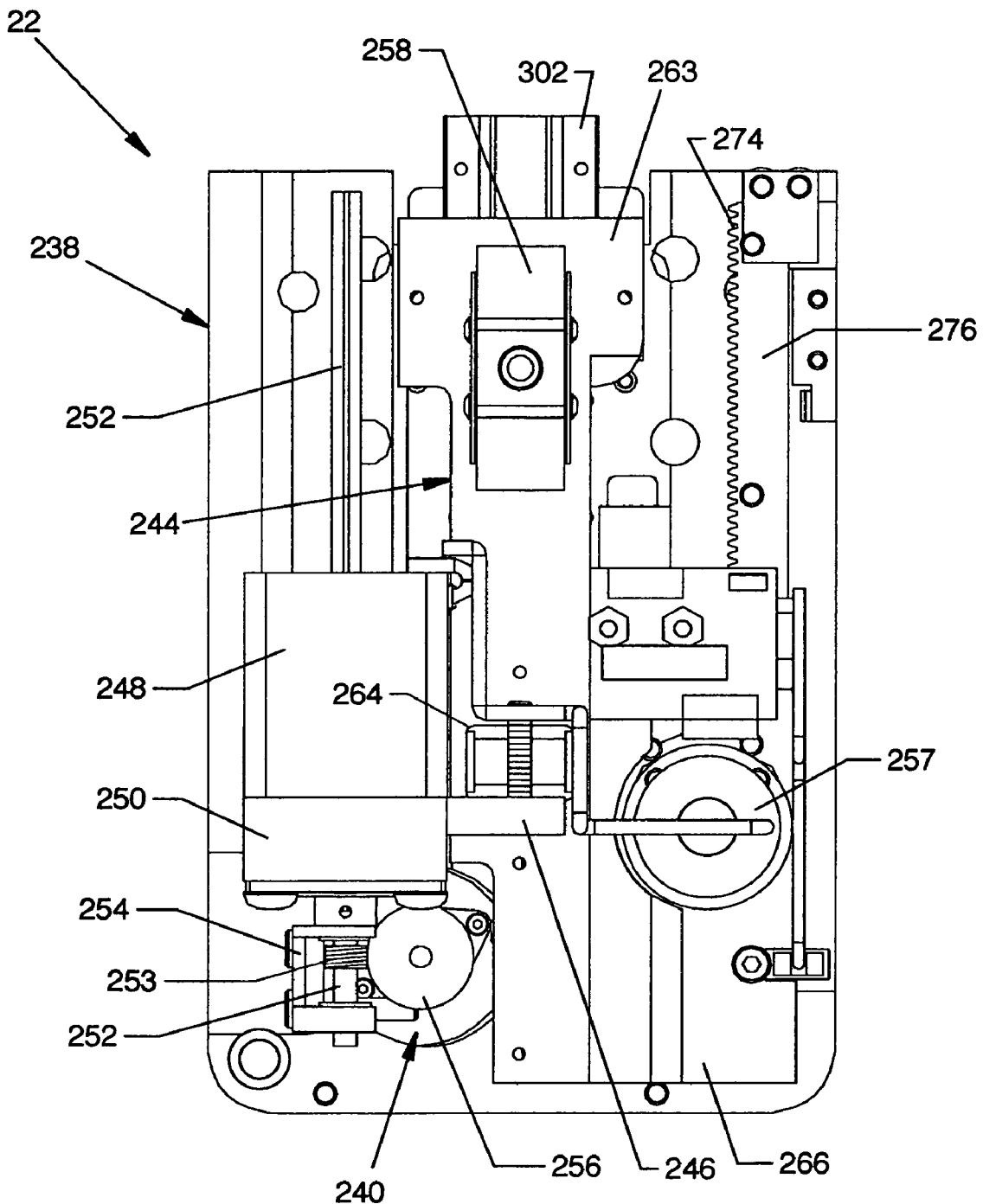
FIG. 16 is a bottom view of the carriage assembly where the bottom mounting plate and the configured bracket have been removed.

FIG. 16 is a bottom view of the carriage assembly 22 where the bottom mounting plate 224 and the configured bracket 242 have been removed for the purposes of brevity and clarity. Shown in particular is the relationship of the pinion shaft 252 and pinion gear 253 to the roller pump drive gear 256.

Figure 17:
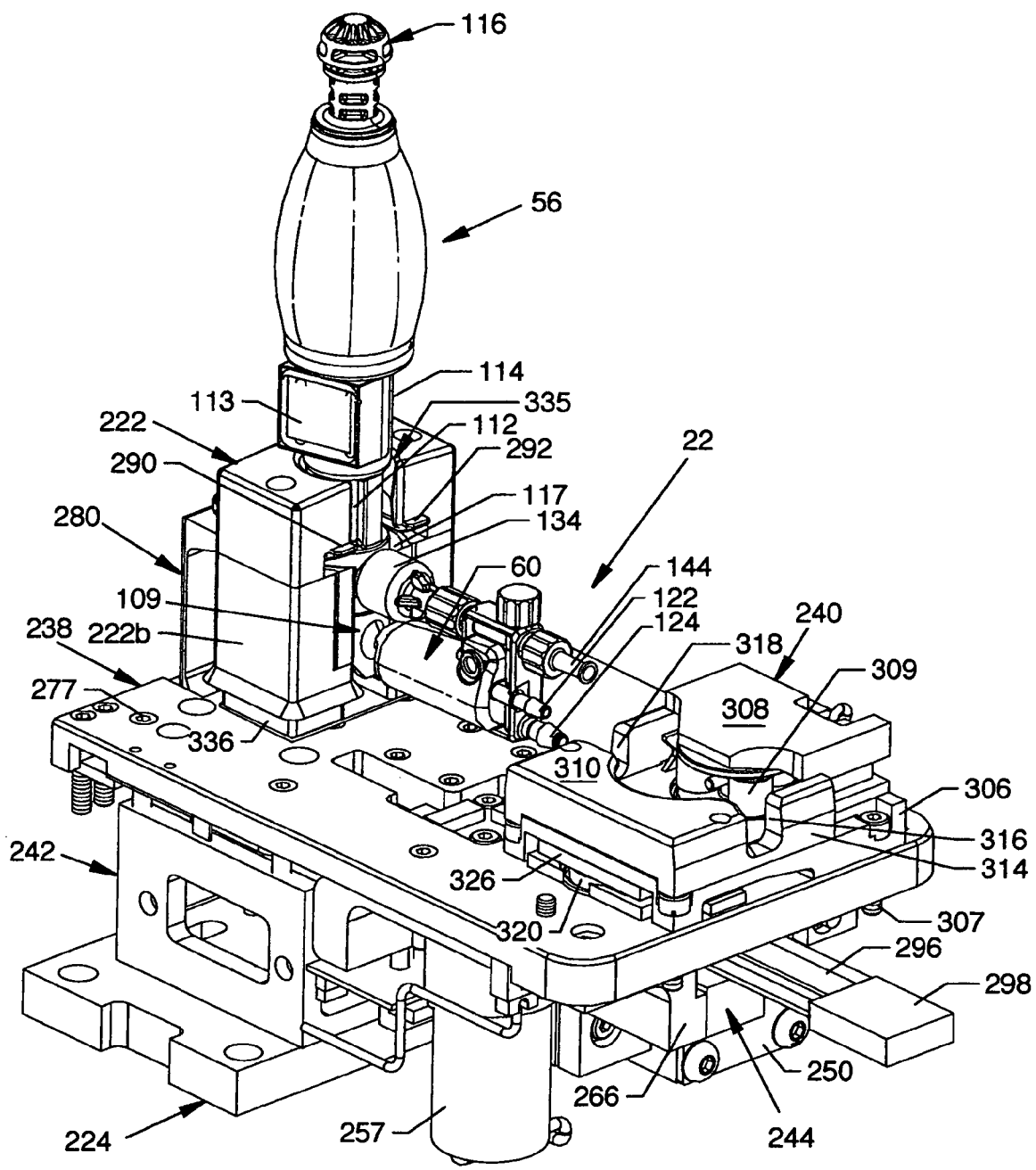
FIG. 17 is an isometric view of the front and one side of the carriage assembly without the cover where the pump is secured thereto.

FIG. 17 is an isometric view of the front and one side of the carriage assembly 22 without the cover 202 where the pump 56 is secured thereto. The positionable tube clamp 310 normally would be actuated along the base 306 to the closed position to capture an effluent waste tube 68, but is shown left open to reveal the roller assembly 309 of the roller pump 240.

Figure 18:
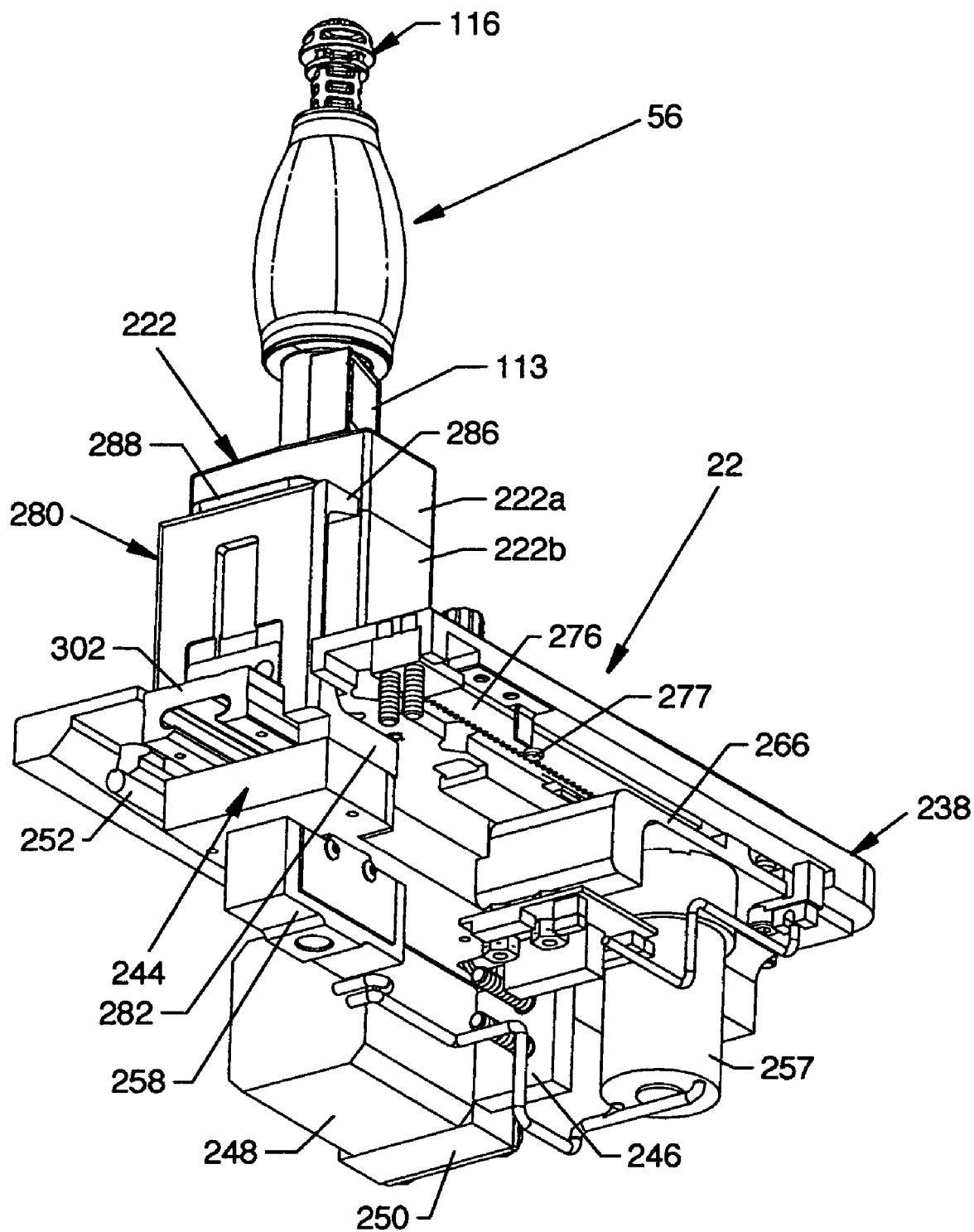
FIG. 18 is an isometric view of the rear and one side of the carriage assembly without the cover where the pump is secured thereto.

FIG. 18 is an isometric view of the rear and one side of the carriage assembly 22 without the cover 202 where the pump 56 is secured thereto. Shown in particular is the relationship of the linear guide 276 connected to the underside of the carriage plate 238, wherein such a relationship is instrumental in the transfer of force from the carriage motor 257 and gear 272 to the carriage plate 238 which is operated along the linear guide 296.

Figure 19:
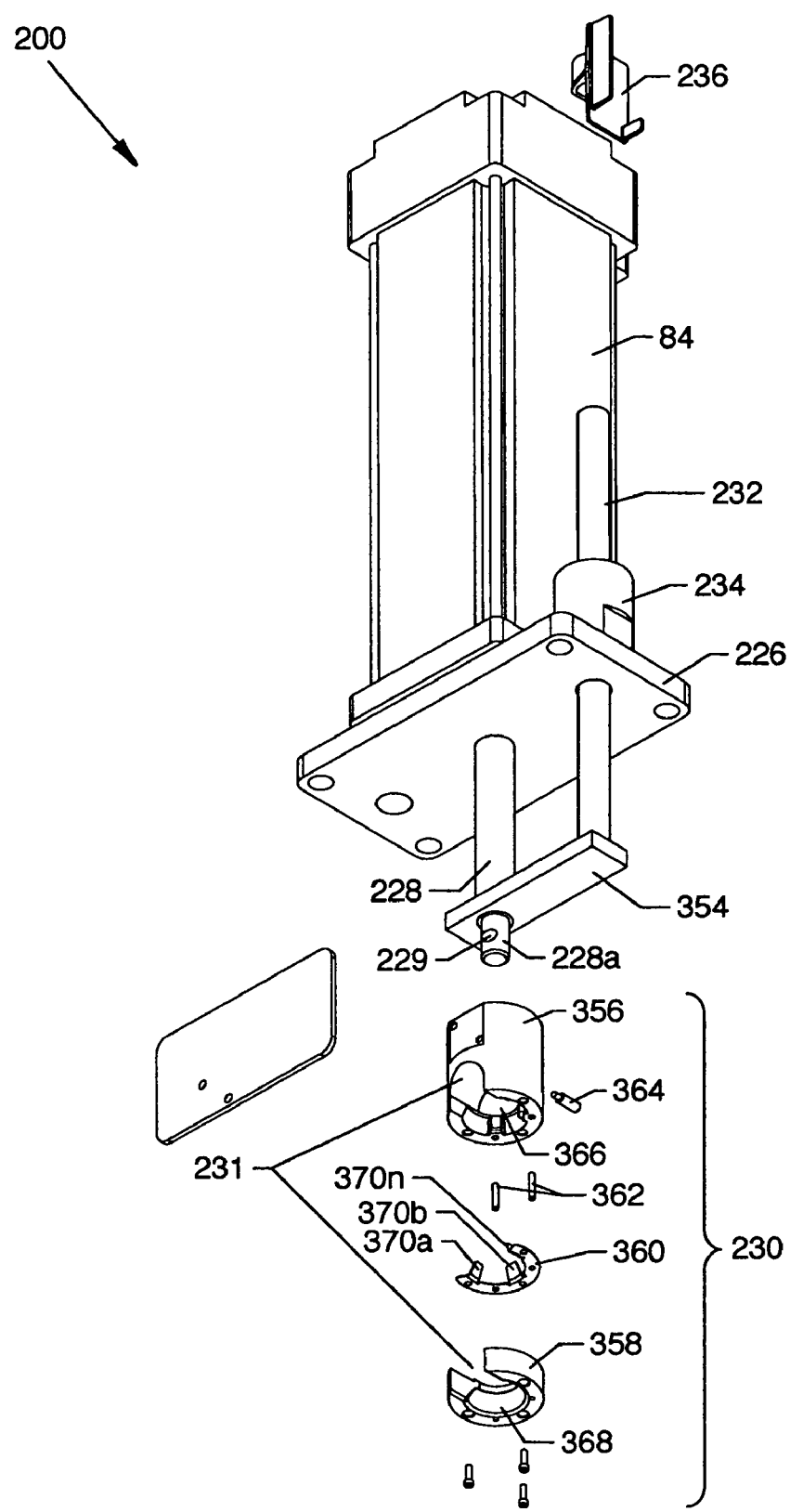
FIG. 19 is an isometric view of the linear actuator assembly and an exploded view of a pump connector.

FIG. 19 is an isometric view of the linear actuator assembly 200 including an exploded view of the pump connector 230 which attaches to the lower region thereof. In addition to the previously shown actuator shaft 228 freely extending through the mounting plate 226, the stroke limit shaft 232, the stroke limit shaft mount 234, and the stop fixture 236 on the upper portion of the stroke limit shaft mount 234, a connector plate 354 is shown connecting the lower part of the stroke limit shaft 232 to the lower region of the actuator shaft 228 at a reduced diameter portion 228a of the actuator shaft 228. The reduced diameter portion 228a of the actuator shaft 228 has a hole 229 therethrough for receipt of a securing device used to couple the actuator shaft 228 to the pump connector 230, as explained fully with reference to FIG. 20.

Figure 20:
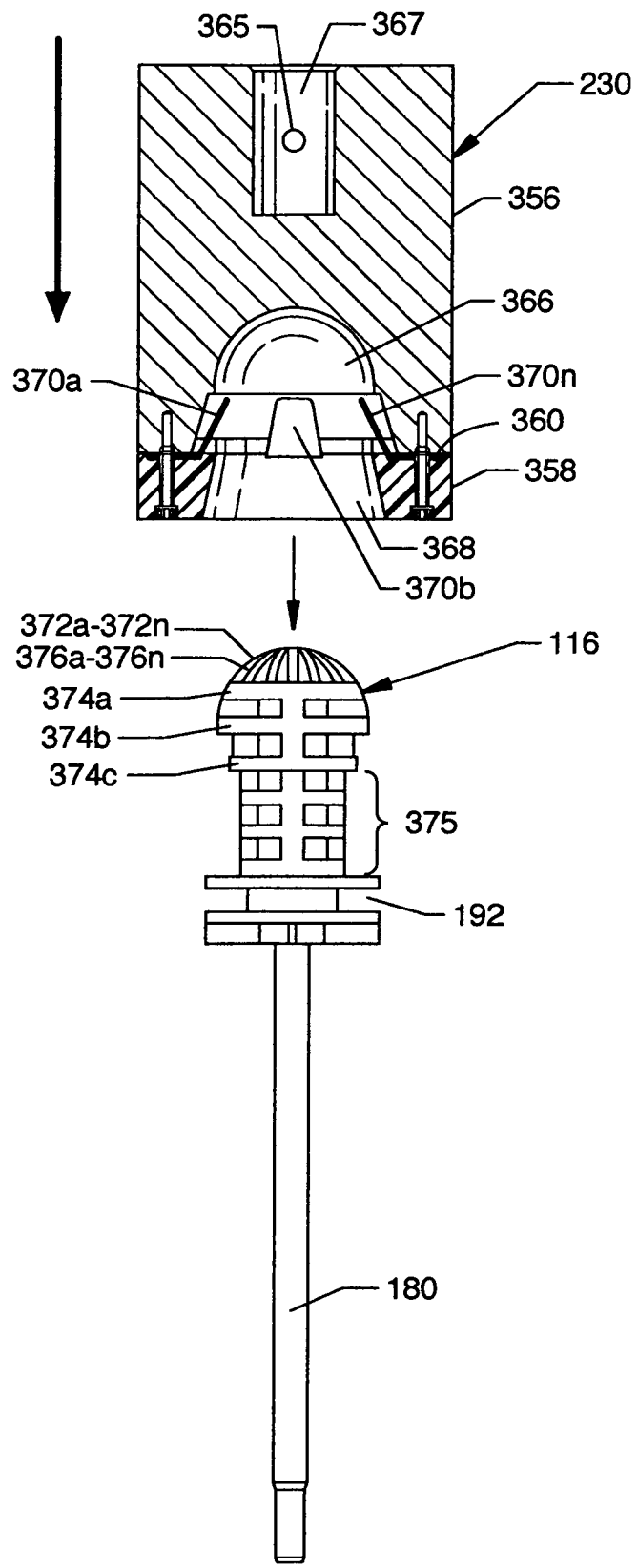
FIG. 20 is a cross section view of the pump connector and a front view of the pump piston head and piston in alignment below the pump connector.

FIG. 20 is a cross section view of the pump connector 230 and a front view of the pump piston head 116 and piston 180 in alignment below the pump connector 230. With reference to FIGS. 19 and 20, the pump connector 230 is now described. The pump connector 230 includes a cylindrically-shaped body 356, a base 358 conforming to the shape of the body 356 for mating thereto, a configured spring plate 360 which is suitably secured between the upper part of the base 358 and the lower portion of the body 356, alignment pins 362, an anti-rotation pin 364, and fastening devices. The body 356 has a centrally located receptor cavity 366 which is a bore terminating as a dome shape. The upper portion of the side opening 231 is in the form of a slot having an arcuate top aligning perpendicular to and intersecting the receptor cavity 366. The base 358 is arcuate in shape and includes a bore 368 which is beveled for guidance of the pump piston head 116 into the receptor cavity 366 and also includes a slot which forms the lower region of the side opening 231. The spring plate 360 is arcuate in shape to conform to the arcuate shape of the base 368 and the lower portion of the body 356 and includes spring pawls 370a-370n extending at an angle upwardly therefrom. The body 356 includes a bore 367 in the center of its top for receiving the reduced diameter portion 228a of the actuator shaft 228. An interrupted hole 365 intersects the bore 367 for alignment with the hole 229 in the reduced diameter portion 228a of the actuator shaft 228 to receive a pin (not shown) or some other type fastening device for affixing the actuator shaft 228 to the body 356.

Figure 24:
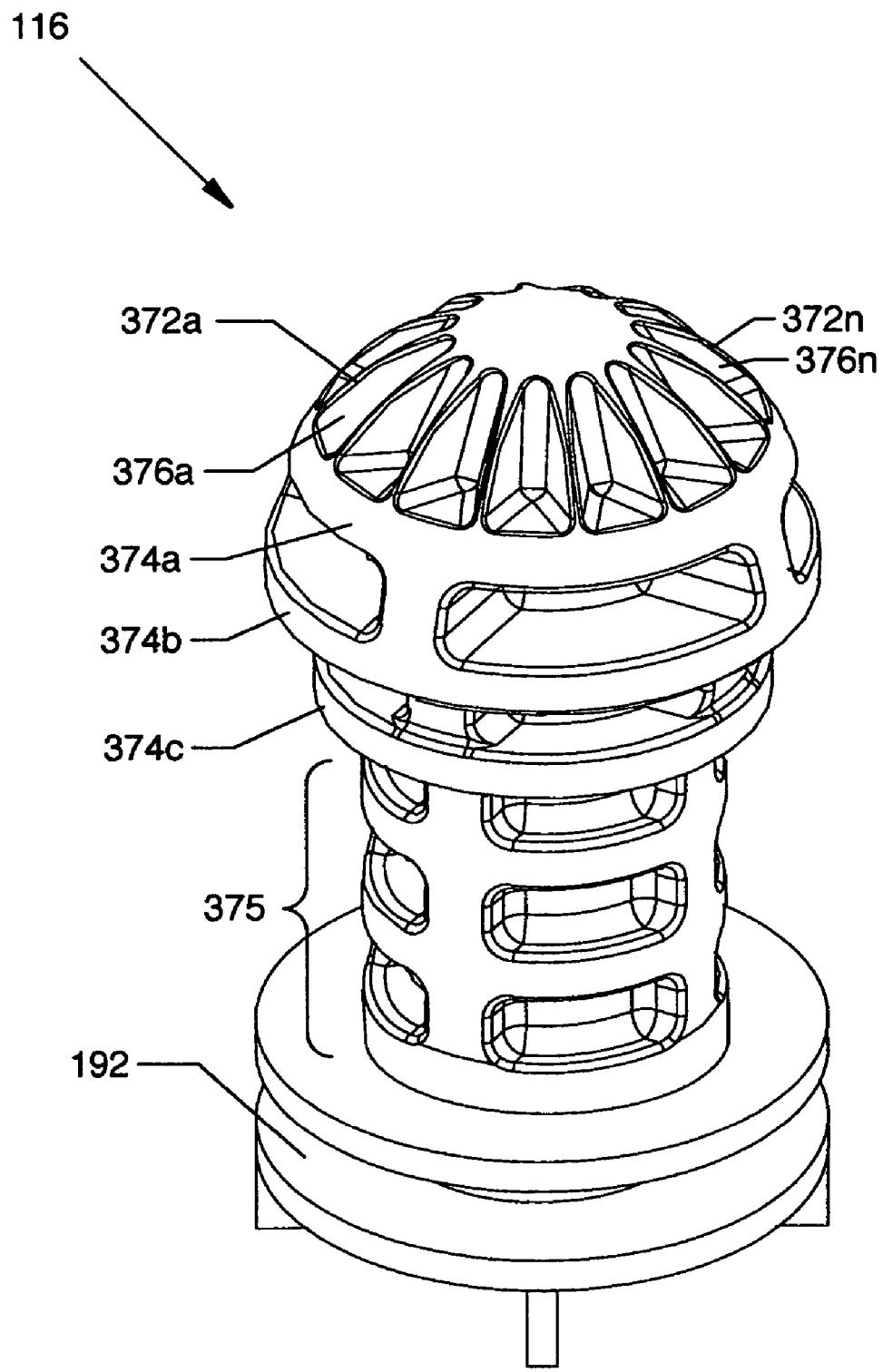
FIG. 24 is an isometric view of the pump piston head showing the relationship of the arcuate ribs to the spaces and of the protuberances to the central body.

The pump piston head 116, which includes material-saving relief structure and is best shown in FIG. 24, includes a top portion which is generally hemispherical in shape to conform with the dome shape of the receptor cavity 366. The generally hemispherical top portion is formed by a plurality of radially aligned arcuate ribs 372a-372n emanating from the top of the pump piston head 116 to meet with the topmost disk-like protuberance 374a of a plurality of horizontally aligned spaced protuberances 374a-374c extending outwardly from above a cylindrically-shaped central body 375 of the pump piston head 116. A plurality of spaces 376a-376n are interspersed between the arcuate ribs 372a-372n. The structure of the arcuate ribs 372a-372n, the spaces 376a-376n, and the upper portion of the protuberance 374a is incorporated to prevent rotation of the pump piston head 116 and piston 180 about the vertical axis thereof as is explained with reference to FIG. 22. Protuberance 374b extends outwardly to exceed the profile presented by the underlying protuberance 374c and is utilized in captured intimate contact in cooperation with the spring pawls 370a-370n, as shown in FIGS. 21 and 22.

Figure 21:
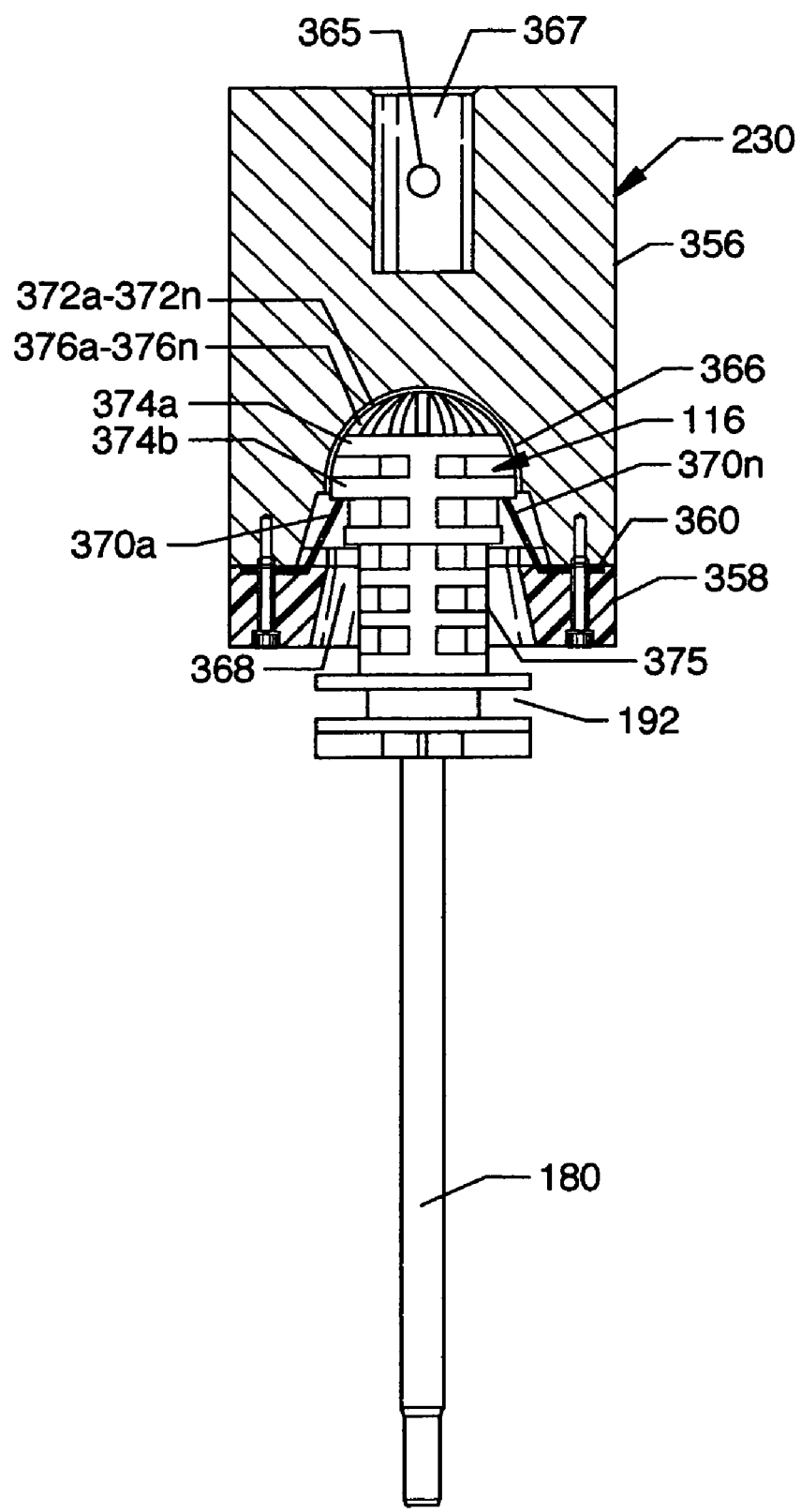
FIG. 21 is a cross section view of the pump connector and a front view of the pump piston head and piston where the pump piston head firmly engages the pump connector.

FIG. 21 is a cross section view of the pump connector 230 and a front view of the pump piston head 116 and piston 180 where the pump piston head 116 is firmly engaged by the pump connector 230. Downward actuation of the actuator shaft 228 causes automatic and secure overhead snap engagement of the pump connector 230 with the pump piston head 116 of the pump 56 for subsequent reciprocating operation of the pump 56 by action of the linear actuator assembly 200. During such engagement, portions of the outwardly facing surface of the protuberance 374a first engage the plurality of spring pawls 370a-370n followed by subsequent disengagement therefrom followed by a second engagement of the plurality of spring pawls 370a-370n by portions of the outwardly facing surface of the protuberance 374b followed by disengagement therefrom followed finally by engagement of the plurality of spring pawls 370a-370n with and against portions of the downwardly facing surface of the protuberance 374b in close proximity to the upper region of the central body 375 at which time the arcuate ribs 372a-372n firmly engage and are held against the dome-like upper structure of the receptor cavity 366.

Figure 22:
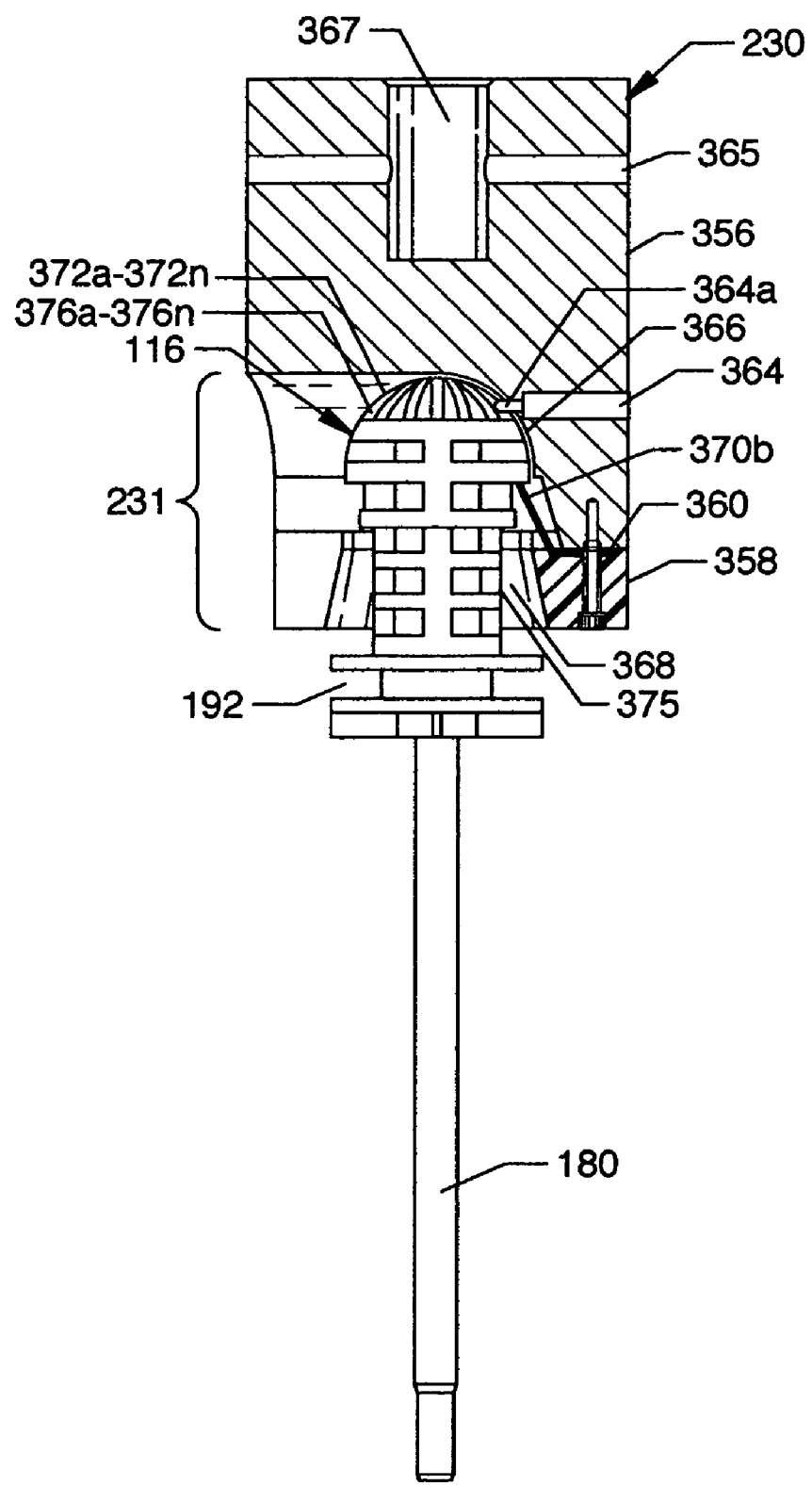
FIG. 22 is a cross section side view of the pump connector and a side view of the pump piston head and piston where the pump piston head firmly engages the pump connector by action of spring pawls.

FIG. 22 is a cross section side view of the pump connector 230 and a side view of the pump piston head 116 and piston 180 where the pump piston head 116 is firmly engaged by the pump connector 230 by action of the spring pawls 370a-370n. Shown in particular is the engagement of a projection 364a extending from the anti-rotation pin 364 located in the body 356 of the pump connector 230 with one of the spaces 376a-376n. Such engagement also places the projection 364a between a consecutive pair of the arcuate ribs 372a-372n, which are thin in shape to divert the rounded end of the projection 364a into one of the spaces 376a-376n. Such an intrusive arrangement serves to prevent rotation of the pump piston head 116 and attached piston 180 about the vertical axis thereof.

Figure 23:
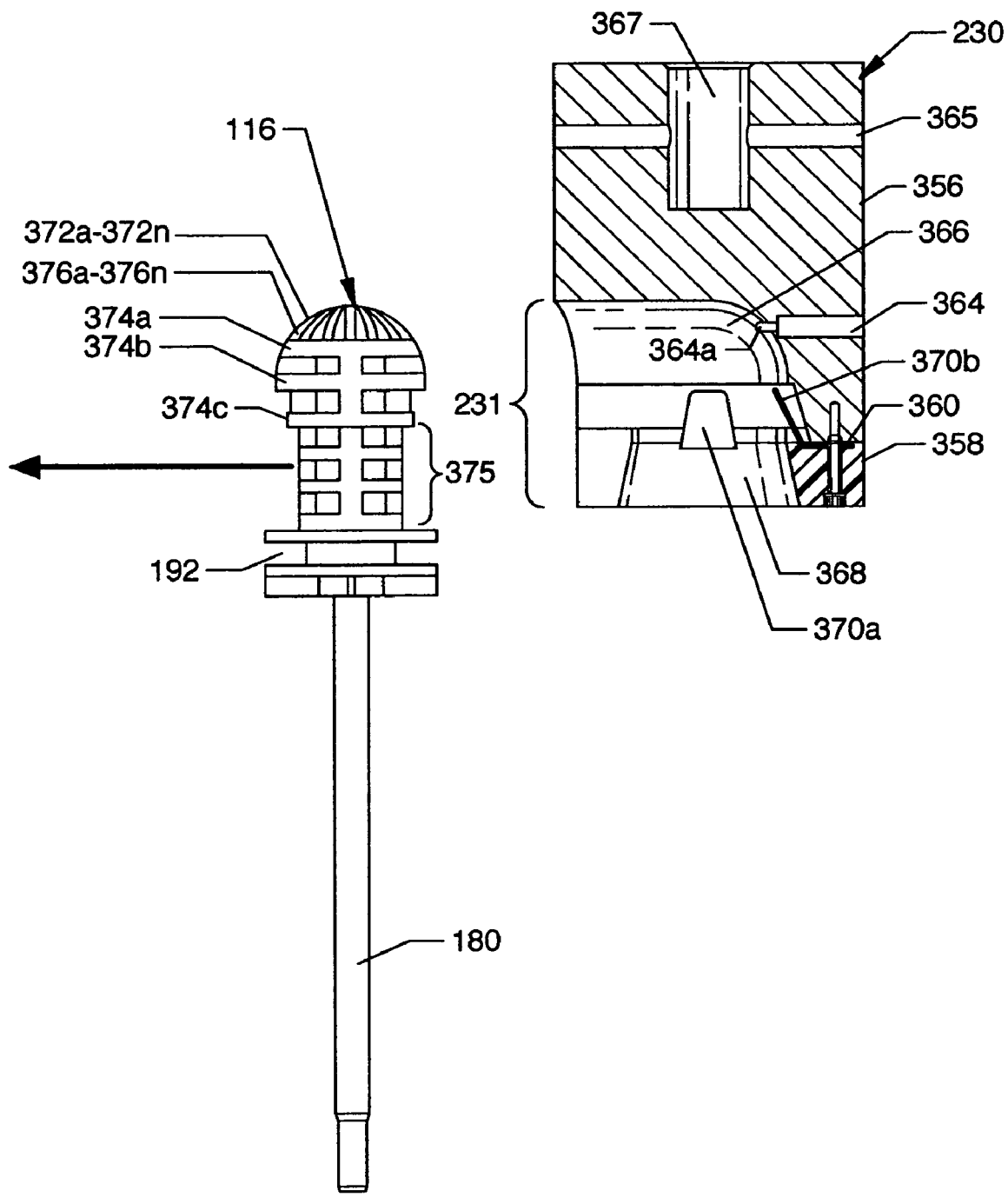
FIG. 23 is a cross section side view of the pump connector and a side view of the pump piston head and piston where the pump piston head has been disengaged from the pump connector.

FIG. 23 is a cross section side view of the pump connector 230 and a side view of the pump piston head 116 and piston 180 where the pump piston head 116 has been disengaged from the pump connector 230. Disengagement of the pump connector 230 from the pump piston head 116 is automatic when the carriage assembly 22 is operated outwardly to the extended open position to cause the pump piston head 116 to exit the pump connector 230 through the side opening 231 in a horizontal motion. The operation of the carriage assembly 22 to the extended open position causes the spring pawls 370a-370n to slidingly disengage the underside of the protuberance 374b.

FIG. 24 is an isometric view of the pump piston head 116 showing the relationship of the arcuate ribs 372a-372n to the spaces 376a-376n and of the protuberances 374a-374c to the central body 375.

FIG. 25 is an isometric view of the pump 56 prior to insertion into and accommodation by the capture block 222 of the carriage assembly 22.

Figure 26:
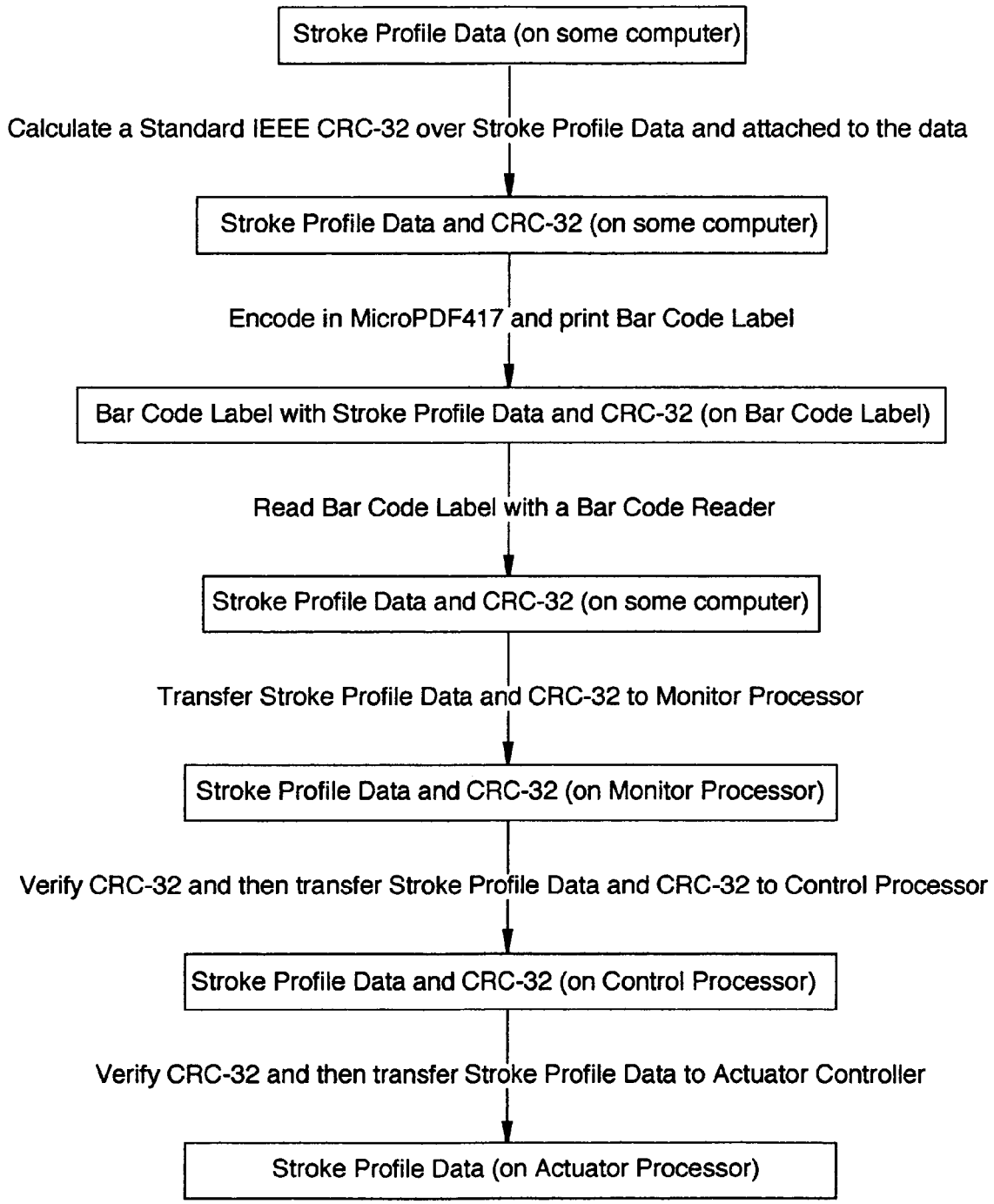

FIG. 26 is a barcode flow chart.

Mode of Operation

Operation of the thrombectomy catheter deployment system 10 utilizes the user interface 32 for controlling the functional operation thereof in conjunction with other components. The thrombectomy catheter deployment system 10 is initiated by opening a sterile package containing the disposable pump/catheter assembly 14 for loading into the drive unit 12. At a suitable time, the carriage assembly 22 is movably actuated to the open position, such as shown in FIG. 25, for acceptance of various components of the pump/catheter assembly 14. The pump 56 aligns to the receptor slot 335 of the capture block 222 and the effluent return tube 66 with the contained high pressure saline supply tube 64 and the effluent waste tube 68 align over and between the tube guides 212 and 214 overlying the roller pump 240. The base 109 of the pump 56 is then urged into engagement with the receptor slot 335 of the capture block 222, such as shown in FIG. 8, and at the same time the effluent waste tube 68 is urged along the angled surfaces 216 and 218 of the tube guides 212 and 214 into the front receptor slot 316 and the rear receptor slot 318 of the open roller pump 240. The effluent return tube 66 with the included high pressure saline supply tube 64 and the saline supply tube 70 are denied entry to the underlying open roller pump 240 by interference of the fixture 140 with the angled surfaces 216 and 218 of the tube guides 212 and 214. During such positioning, the effluent collection bag 28 is automatically and supportively placed in the combined drip tray 24 and receptacle 26. The saline supply bag 72 containing heparinized saline can be spiked prior to or subsequent to loading the pump 56 and suitably positioned, such as on the saline bag hook 34 or 36. The carriage motor 257 is then energized by depressing the carriage assembly activation switch 30 to movably actuate the carriage plate 238 and the cover 202 to the closed position, whereby further capturing of the effluent waste tube 68 and of the pump 56 occur. During such movably actuated capturings, the positionable tube clamp 310 is advanced to automatically and forcibly engage the effluent waste tube 68 for use in the roller pump 240, and the pump 56 is automatically captured in the receptor slot 335 of the capture block 222. Capture of the pump 56 in the receptor slot 335 of the capture block 222 occurs during inwardly directed advancement of the carriage plate 238 when the slots 330 and 332 of the capture block 222 engage the capture tabs 290 and 292 of the capture clip 288 at which time simultaneous engagement of the annular surface 117 of the pump 56 by the capture tabs 290 and 292 occurs. Capturing of the pump 56 provides for secure and stable mounting and support of the pump 56 and the components directly associated with the pump 56, such as, but not limited to, the bubble trap 60, the connection manifold assembly 62 and proximal ends of the effluent waste 68, the saline supply tube 70, the effluent return tube 66, and other associated structure. When the carriage plate 238 is movably actuated to the fully advanced closed position, the barcode reader assembly 86 senses individualized data regarding each particular and individual pump 56 located on the data plate 113 of any pump 56 which is utilized to facilitate tailored operation of the reciprocating linear actuator 84 and/or other components essential to best and proper operation of each particular and individual pump 56. When the carriage plate 238 is movably actuated to the fully advanced closed position, the reciprocating linear actuator 84 is energized as required to cause the pump connector to descend downwardly in vertically directed motion to engage and capture the pump piston head 116, as described with reference to FIGS. 21 and 22. At an appropriate time, the tip of the thrombectomy catheter 58 is placed in a bowl of sterile saline and the pump 56 is operated by action of the reciprocating linear actuator 84 to prime the thrombectomy catheter 58. Medical personnel insert the thrombectomy catheter 58 into the patient at a convenient time, and operation of the thrombectomy catheter deployment system 10 incorporating the user interface 32 and the foot switch 95 can begin, as desired. The reciprocating linear actuator 84 is actuated according to the operating parameters as sensed by the barcode reader assembly 86 to influence proper saline pressures, pump speed, flow rates, and the like to operate the pump 56 to deliver pressurized saline to the thrombectomy catheter 58 via the high pressure saline supply tube 64 residing in the effluent return tube 66. Supply saline is routed through the bubble trap 60 and highly pressurized by the pump 56, as previously described, and through the high pressure saline supply tube 64 to the thrombectomy catheter 58 for use in a thrombectomy or other related procedure. Effluent is returned through the effluent return tube 66 to the connection manifold assembly 62 for collection in the effluent collection bag 28 through the roller pump controlled effluent waste tube 68. When the thrombectomy procedure is complete, the carriage plate 238 is movably actuated outwardly to the open position for manual removal of the components of the pump/catheter assembly 14. During movable actuation outwardly to the open position, the positionable tube clamp 310 is repositioned to cause release of the effluent waste tube 68 from the roller pump 240, and the pump piston head 116 is slidingly disengaged from the pump connector 230 in a horizontal direction through the side opening 231, as described with reference to FIG. 23.

Various modifications can be made to the present invention without departing from the apparent scope thereof.

| THROMBECTOMY CATHETER DEPLOYMENT SYSTEM PARTS LIST | |
|---|---|
| 10 | thrombectomy catheter deployment system |
| 12 | drive unit |
| 14 | pump/catheter assembly |
| 16a-n | panels |
| 18 | door |
| 20 | door |
| 22 | carriage assembly |
| 24 | drip tray |
| 26 | removable receptacle |
| 28 | effluent collection bag |
| 30 | carriage assembly activation switch |
| 32 | user interface |
| 34 | saline bag hook |
| 36 | saline bag hook |
| 38 | mounting pad |
| 40 | mounting pad |
| 42 | handle |
| 44 | mounting pad |
| 46 | mounting pad |
| 48 | mounting pad |
| 50 | mounting pad |
| 52a-n | wheels |
| 54 | brake pedal |
| 55 | brake pedal |
| 56 | pump |
| 58 | thrombectomy catheter |
| 60 | bubble trap |
| 60a | bubble trap half |
| 60b | bubble trap half |
| 62 | connection manifold assembly |
| 64 | high pressure saline supply tube |
| 66 | effluent return tube |

THROMBECTOMY CATHETER DEPLOYMENT SYSTEM
PARTS LIST

| | |
|---|---|
| 68 | effluent waste tube |
| 69 | transition fixture |
| 70 | saline supply tube |
| 71 | bag spike |
| 72 | saline supply bag |
| 74 | splash guard |
| 75 | aperture |
| 76a-d | support structures |
| 78 | base |
| 80 | panel |
| 82 | panel |
| 84 | reciprocating linear actuator |
| 86 | barcode reader assembly |
| 87 | mirror |
| 88 | isolation transformer |
| 90 | power supply |
| 92 | linear actuator controller |
| 94 | rear access panel |
| 95 | foot switch |
| 96 | foot switch holder |
| 98 | hanger |
| 100 | electrical supply cord |
| 102 | foot switch cord |
| 104 | rear connector chassis |
| 106 | fan cavity |
| 108 | panel |
| 109 | base |
| 110 | upper portion |
| 111 | geometrically configured lower portion |
| 112 | tubular body |
| 113 | data plate |
| 114 | top body |
| 115 | connecting panel |
| 116 | pump piston head |
| 117 | annular surface |
| 118 | flexible boot |
| 120 | bracket |
| 122 | saline inlet port |
| 124 | effluent outlet port |
| 126 | effluent return port |
| 128 | auxiliary port |
| 130 | cap |
| 132 | connector |
| 134 | connector |
| 136 | hydrophobic filter |
| 138 | hydrophobic filter |
| 140 | fixture |
| 141a-b | tabs |
| 142 | connector |
| 144 | connection tube |
| 148 | tubular manifold |
| 150 | passage port |
| 151 | lumen |
| 152 | high pressure fitting |
| 154 | connection port |
| 156 | pump saline inlet port |
| 158 | receptor port |
| 159 | seal |

THROMBECTOMY CATHETER DEPLOYMENT SYSTEM
PARTS LIST

| | |
|---|---|
| 160 | baffle |
| 162 | interior cavity |
| 164 | arcuate baffle |
| 170 | cylinder |
| 171 | inner wall |
| 172 | check ball seat |
| 174 | inlet check ball |
| 176 | passage |
| 178 | receptor |
| 180 | piston |
| 182 | threaded insert |
| 184 | body hole |
| 186 | high pressure seal |
| 188 | silicone seal |
| 190 | annular boot mounting groove |
| 192 | annular boot mounting groove |
| 200 | linear actuator assembly |
| 202 | cover |
| 203 | bottom cover |
| 208 | cam |
| 210 | cam |
| 212 | tube guide |
| 214 | tube guide |
| 216 | angled surface |
| 218 | angled surface |
| 220 | channel |
| 222 | capture block |
| 222a | capture block top |
| 222b | capture block bottom |
| 224 | bottom mounting plate |
| 226 | mounting plate |
| 228 | actuator shaft |
| 228a | reduced diameter portion |
| 229 | hole |
| 230 | pump connector |
| 231 | side opening |
| 232 | stroke limit shaft |
| 234 | stroke limit shaft mount |
| 236 | stop fixture |
| 238 | carriage plate |
| 240 | roller pump |
| 242 | configured bracket |
| 244 | top mounting plate |
| 246 | mounting flange |
| 247 | pivot flange |
| 248 | roller pump motor |
| 250 | gear drive |
| 251 | pinion shaft support |
| 252 | pinion shaft |
| 253 | pinion gear |
| 254 | pinion shaft end bracket |
| 255 | screw |
| 256 | roller pump drive gear |
| 257 | carriage motor |
| 258 | load cell |
| 259 | adjustable stop |
| 260 | recessed hole |
| 261 | screw |
| 262 | screw |
| 263 | wide portion (of 244) |
| 264 | aperture |
| 265 | pivot bushings |

THROMBECTOMY CATHETER DEPLOYMENT SYSTEM PARTS LIST -continued

| | | |
|---|---|---|
| 266 | carriage motor mounting plate | |
| 267 | bore | |
| 268 | aperture | |
| 270 | hole | |
| 271 | hole | |
| 272 | gear | |
| 273 | pin | |
| 274 | teeth | |
| 275 | hole | |
| 276 | linear guide | |
| 277 | screw | |
| 278 | cam post | |
| 280 | capture clip mounting bracket | |
| 282 | foot | |
| 284 | foot | |
| 286 | top plate | |
| 288 | capture clip | |
| 289 | fastener | |
| 290 | capture tab | |
| 292 | capture tab | |
| 294 | slot | |
| 296 | linear guide | |
| 298 | stop block | |
| 300 | front truck | |
| 302 | rear truck | |
| 304 | opening | |
| 305 | cam assembly cavity | |
| 306 | base | |
| 307 | screw | |
| 308 | roller cover | |
| 309 | roller assembly | |
| 310 | outside race or platen | |
| 312 | arcuate surface | |
| 314 | front guide | |
| 315 | rear guide | |
| 316 | front receptor slot | |
| 318 | rear receptor slot | |
| 320 | cam assembly | |
| 322 | slotted tab | |
| 324 | cam assembly mount | |
| 326 | rotating cam post assembly | |
| 328 | arcuate surface | |
| 330 | slot | |
| 332 | slot | |
| 334 | arcuate surface | |
| 335 | receptor slot | |
| 336 | left skirted base | |
| 338 | right skirted base | |
| 340 | aperture | |
| 342 | aperture | |
| 344 | spacer plate | |
| 346 | pin | |
| 348 | pin | |
| 350 | fastener screw | |
| 352 | fastener screw | |
| 354 | connector plate | |
| 356 | body | |
| 358 | base | |
| 360 | spring plate | |
| 362 | alignment pin | |
| 364 | anti-rotation pin | |
| 364a | projection | |
| 365 | interrupted hole | |
| 366 | receptor cavity | |
| 367 | bore | |
| 368 | beveled bore | |
| 370a-n | spring pawls | |
| 372a-n | arcuate ribs | |
| 374a-c | protuberances | |
| 375 | central body | |
| 376a-n | spaces | |

It is claimed:

1. A thrombectomy catheter deployment system comprising:
a. a drive unit having a digitally controlled mode; a carriage assembly having capture tabs; and a pump connector having a dome-shaped receptor cavity and a retractable pin; and,
b. a thrombectomy catheter assembly comprising a combination of a pump and catheter, said combination being rigidly coupled to each other such that the combination is loaded into the drive unit as a single unitary item; said pump having a base with an upper portion and a lower portion, the upper portion also comprising an annular surface that mates with the capture tabs of the carriage assembly; said pump further comprising a piston head having a generally hemispherical top portion with at least two arcuate ribs forming a space therebetween, said top portion adapted to mate with said dome-shaped receptor cavity; wherein said pin is capable of deploying into the space.

2. The thrombectomy catheter deployment system of claim 1, wherein operating information from the thrombectomy catheter assembly determines the digitally controlled mode of the drive unit.

3. The thrombectomy catheter deployment system of claim 2, wherein the operating information is in a barcode, and wherein the drive unit includes a barcode reader, such that the operating information in the barcode determines and controls the digitally controlled mode of the drive unit.

4. The thrombectomy catheter deployment system of claim 2, wherein the operating information is in a radio frequency identification technology code, and wherein the drive unit includes a radio frequency identification technology code reader, such that the operating information in the radio frequency technology code determines and controls the digitally controlled mode of the drive unit.

5. The thrombectomy catheter deployment system of claim 2, wherein the thrombectomy catheter assembly cannot be operatively loaded in the drive unit without the information carried by the thrombectomy catheter assembly.

6. The thrombectomy catheter deployment system of claim 1, wherein the drive unit includes a capture block and a reciprocating linear actuator, and wherein loading of the thrombectomy catheter assembly into the capture block results in automatic engagement of the reciprocating linear actuator with the pump piston head.

7. The thrombectomy catheter deployment system of claim 6, wherein the drive unit awaits operator intervention to load the thrombectomy catheter assembly from the capture block.

8. The thrombectomy catheter deployment system of claim 7, wherein the operator intervention is supplying power to the drive unit.

9. The thrombectomy catheter deployment system of claim 1, wherein the drive unit includes a capture block and an effluent bag support, and wherein the thrombectomy catheter assembly includes an effluent bag, and wherein loading of the thrombectomy catheter assembly into the capture block results in automatic positioning of the effluent bag in the effluent bag support.

10. The thrombectomy catheter deployment system of claim 1, wherein the drive unit includes a capture block and a roller pump, and wherein the thrombectomy catheter assembly includes an effluent waste tube engageable by the roller pump, and wherein loading of the thrombectomy catheter assembly into the capture block results in automatic positioning of the effluent waste tube into the roller pump.

11. The thrombectomy catheter deployment system of claim 1, wherein the pump of the thrombectomy catheter assembly is an insert molded pump.

12. The thrombectomy catheter deployment system of claim 1, wherein the pump of the thrombectomy catheter assembly is an insert molded pump with a check valve having a plastic seat and stainless steel check ball.

13. The thrombectomy catheter deployment system of claim 1, wherein the thrombectomy catheter assembly is disposable.

14. The thrombectomy catheter deployment system of claim 1, wherein the thrombectomy catheter assembly loaded in the drive unit causes isovolumetric flow during thrombectomy.

15. The thrombectomy catheter deployment system of claim 1, wherein the drive unit includes a reciprocating linear actuator, a roller pump, a capture block and means for reading operating information from the thrombectomy catheter assembly, and wherein the pump is an insert molded pump with a plastic check ball seat and a stainless steel check ball, said thrombectomy catheter assembly further comprising an effluent waste tube, a bubble trap, a thrombectomy catheter and encryption of the information, and wherein loading of the thrombectomy catheter assembly into the capture block results in thrombectomy catheter deployment without operator intervention except spiking a reservoir of fluid.

16. A thrombectomy catheter deployment system comprising:
  a. a reusable drive unit having a digitally controlled mode; a carriage assembly having capture tabs; and a pump connector having a dome-shaped receptor cavity and a retractable pin; and,
  b. a plurality of disposable catheter assemblies, each of the disposable catheter assemblies comprising at least a pump and a thrombectomy catheter that are preconnected and carrying encrypted digital control instructions, said pump having a base with an upper portion and a lower portion, the upper portion also comprising an annular surface that mates with the capture tabs of the carriage assembly; said pump further comprising a piston head having a generally hemispherical top portion with at least two arcuate ribs forming a space therebetween, said top portion adapted to mate with said dome-shaped receptor cavity; wherein said pin is capable of deploying into the space, the encrypted digital control instructions enabling automatic loading by the reusable drive unit and, subsequent to deployment, controlling the mode of isovolumetric flow by the resulting deployed thrombectomy catheter.

17. The thrombectomy catheter deployment system of claim 16, wherein the encrypted digital control instructions of each disposable catheter assembly include properties of each disposable assembly and are coordinated with the reusable drive unit.

18. The thrombectomy catheter deployment system of claim 17, wherein the plurality of disposable catheter assemblies includes at least one disposable catheter assembly carrying encrypted digital control instructions distinct from the encrypted digital control instructions of another disposable catheter assembly of the plurality.

19. The thrombectomy catheter deployment system of claim 18, wherein the at least one disposable catheter assembly carrying encrypted digital control instructions distinct from the encrypted digital control instructions of another disposable catheter assembly represents a difference in manufacturing tolerances.

20. The thrombectomy catheter deployment system of claim 18, wherein the at least one disposable catheter assembly carrying encrypted digital control instructions distinct from the encrypted digital control instructions of another disposable catheter assembly represents an intended difference in dimensions and not a difference in manufacturing tolerances.

21. The thrombectomy catheter deployment system of claim 20, wherein the at least one disposable catheter assembly carrying encrypted digital control instructions distinct from the encrypted digital control instructions of another disposable catheter assembly representing an intended difference in dimensions further includes operator readable indicia to facilitate selection of the disposable catheter assembly enabling a desired distinct mode on the drive unit when the thrombectomy catheter is deployed.

* * * * *

UNITED STATES PATENT AND TRADEMARK OFFICE
CERTIFICATE OF CORRECTION

| | | |
|---|---|---|
| PATENT NO. | : 7,935,077 B2 | Page 1 of 1 |
| APPLICATION NO. | : 11/237558 | |
| DATED | : May 3, 2011 | |
| INVENTOR(S) | : Thor et al. | |

It is certified that error appears in the above-identified patent and that said Letters Patent is hereby corrected as shown below:

On the Title Page, item (75), under "Inventors", in Column 1, Lines 10-11,
delete "Mark Alfred Hilse, Ham Lake, MN (US);".

Signed and Sealed this
Twenty-third Day of April, 2013

Teresa Stanek Rea
*Acting Director of the United States Patent and Trademark Office*